(12) United States Patent
Remijan et al.

(10) Patent No.: US 8,317,689 B1
(45) Date of Patent: Nov. 27, 2012

(54) MINIATURE ENDOSCOPE SYSTEM

(75) Inventors: Paul Remijan, Holland, MA (US);
Denis LaBombard, Georgetown, MA (US)

(73) Assignee: Visionscope Technologies LLC, Portsmouth, NH (US)

( * ) Notice: Subject to any disclaimer, the term of this patent is extended or adjusted under 35 U.S.C. 154(b) by 0 days.

(21) Appl. No.: 09/660,840

(22) Filed: Sep. 13, 2000

Related U.S. Application Data

(63) Continuation-in-part of application No. 09/518,954, filed on Mar. 6, 2000.

(60) Provisional application No. 60/212,935, filed on Jun. 20, 2000, provisional application No. 60/187,305, filed on Mar. 6, 2000, provisional application No. 60/156,478, filed on Sep. 28, 1999, provisional application No. 60/153,568, filed on Sep. 13, 1999.

(51) Int. Cl.
*A61B 1/00* (2006.01)
*A61B 1/04* (2006.01)
*A61B 1/07* (2006.01)

(52) U.S. Cl. ........ 600/182; 600/112; 600/125; 600/130; 600/177; 600/178; 600/179; 600/131

(58) Field of Classification Search .................. 600/101, 600/112, 114, 121, 125, 130, 136, 138, 160, 600/176, 178, 179, 182
See application file for complete search history.

(56) References Cited

U.S. PATENT DOCUMENTS

| | | | |
|---|---|---|---|
| 1,692,554 A * | 11/1928 | Leiter | 600/178 |
| 3,261,349 A | 7/1966 | Wallace | |
| 3,724,922 A * | 4/1973 | Jones | 356/241.1 |
| 3,784,386 A * | 1/1974 | Araujo et al. | 501/13 |
| 3,902,880 A * | 9/1975 | Strack | 65/410 |
| 3,941,121 A * | 3/1976 | Olinger et al. | 600/167 |
| 4,254,762 A * | 3/1981 | Yoon | 600/114 |
| 4,569,334 A * | 2/1986 | Ohshiro | 600/182 |
| 4,593,973 A * | 6/1986 | Yoshida et al. | 385/126 |
| 4,607,622 A | 8/1986 | Fritch et al. | |
| 4,610,242 A * | 9/1986 | Santangelo et al. | 600/114 |
| 4,641,912 A * | 2/1987 | Goldenberg | 385/43 |
| 4,755,029 A | 7/1988 | Okabe | |

(Continued)

FOREIGN PATENT DOCUMENTS

DE     88 14 573.5     1/1990

(Continued)

OTHER PUBLICATIONS

Rol, P. et al., "Optical Properties of Miniaturized Endoscopes for Ophthalmic Use", *Optical Engineering*, vol. 34, No. 7, pp. 2070-2077, Jul. 1995.

*Primary Examiner* — John P Leubecker
(74) *Attorney, Agent, or Firm* — McCarter & English LLP

(57) ABSTRACT

The present invention relates to a small diameter endoscope in which a handle is removably attached to a probe. The probe includes a fiber optic illumination channel that is concentric about an imaging channel. The handle includes an imaging device that detects light from the imaging channel and a sterile barrier that can be extended over the handle for use. Relay optics couples the small diameter imaging channel to the imaging device in the handle. The probe has a mounting hub that connects the probe to the handle and also serves to optically couple the fiber optic illumination channel to a light source.

42 Claims, 20 Drawing Sheets

U.S. PATENT DOCUMENTS

| | | | |
|---|---|---|---|
| 4,790,295 A * | 12/1988 | Tashiro | 600/176 |
| 4,802,461 A | 2/1989 | Cho | |
| 4,807,597 A * | 2/1989 | Tsuno et al. | 600/177 |
| 4,854,302 A | 8/1989 | Allred, III | 128/6 |
| 4,878,485 A | 11/1989 | Adair | |
| 4,904,246 A | 2/1990 | Atkinson | |
| 4,921,326 A | 5/1990 | Wild et al. | 350/96.26 |
| 4,947,245 A | 8/1990 | Ogawa et al. | |
| 4,963,960 A * | 10/1990 | Takami | 348/69 |
| 4,972,827 A * | 11/1990 | Kishi et al. | 604/164.09 |
| 4,979,498 A | 12/1990 | Oneda et al. | |
| 5,074,642 A | 12/1991 | Hicks | |
| 5,121,740 A | 6/1992 | Uram | |
| 5,156,142 A | 10/1992 | Anapliotis et al. | |
| 5,159,919 A | 11/1992 | Chikama | |
| 5,168,863 A * | 12/1992 | Kurtzer | 600/122 |
| 5,172,685 A | 12/1992 | Nudelman | |
| 5,183,031 A * | 2/1993 | Rossoff | 600/131 |
| 5,184,602 A * | 2/1993 | Anapliotis et al. | 600/137 |
| 5,237,984 A | 8/1993 | Williams, III et al. | |
| 5,274,500 A | 12/1993 | Dunn | |
| 5,290,279 A | 3/1994 | Bonati et al. | |
| 5,319,731 A * | 6/1994 | Eastman | 385/115 |
| 5,323,766 A | 6/1994 | Uram | |
| 5,323,767 A * | 6/1994 | Lafferty et al. | 600/109 |
| 5,329,936 A * | 7/1994 | Lafferty et al. | 600/109 |
| 5,337,734 A | 8/1994 | Saab | |
| 5,341,240 A | 8/1994 | Broome | |
| 5,347,990 A | 9/1994 | Ebling et al. | |
| 5,369,525 A | 11/1994 | Bala et al. | |
| 5,402,768 A | 4/1995 | Adair | |
| 5,406,938 A | 4/1995 | Mersch et al. | |
| 5,413,092 A | 5/1995 | Williams, III et al. | |
| 5,423,312 A * | 6/1995 | Siegmund et al. | 600/109 |
| 5,425,123 A * | 6/1995 | Hicks | 385/117 |
| 5,458,132 A | 10/1995 | Yabe et al. | |
| 5,467,762 A * | 11/1995 | Sauer et al. | 600/114 |
| 5,476,090 A | 12/1995 | Kishi | |
| 5,479,550 A * | 12/1995 | Nishioka et al. | 385/116 |
| 5,483,951 A | 1/1996 | Frassica et al. | |
| 5,486,155 A | 1/1996 | Muller et al. | 600/137 |
| 5,496,259 A | 3/1996 | Perkins | |
| 5,538,497 A | 7/1996 | Hori | |
| 5,569,161 A | 10/1996 | Ebling et al. | |
| 5,573,493 A | 11/1996 | Sauer et al. | |
| 5,575,757 A | 11/1996 | Kenedy | |
| 5,587,839 A | 12/1996 | Miyano et al. | |
| 5,591,160 A | 1/1997 | Reynard | |
| 5,591,192 A | 1/1997 | Privitera et al. | |
| 5,599,278 A | 2/1997 | Hibbard | |
| 5,601,525 A * | 2/1997 | Okada | 600/160 |
| 5,617,498 A | 4/1997 | Cawood | |
| 5,630,783 A * | 5/1997 | Steinberg | 600/158 |
| 5,630,784 A | 5/1997 | Siegmund et al. | |
| 5,630,788 A | 5/1997 | Forkner et al. | |
| 5,685,822 A | 11/1997 | Harhen | |
| 5,690,605 A | 11/1997 | Hamlin et al. | |
| 5,700,236 A | 12/1997 | Sauer et al. | |
| 5,702,348 A | 12/1997 | Harhen | |
| 5,704,892 A | 1/1998 | Adair | |
| 5,746,494 A * | 5/1998 | Koeda et al. | 362/560 |
| 5,751,341 A | 5/1998 | Chaleki et al. | |
| 5,754,716 A * | 5/1998 | Kim et al. | 385/28 |
| 5,776,049 A | 7/1998 | Takahashi | |
| 5,788,628 A | 8/1998 | Matsuno et al. | |
| 5,800,343 A * | 9/1998 | Takeuchi et al. | 600/132 |
| 5,817,015 A | 10/1998 | Adair | |
| 5,827,177 A | 10/1998 | Oneda et al. | |
| 5,876,329 A | 3/1999 | Harhen | |
| 5,879,287 A | 3/1999 | Yoshihashi | |
| 5,879,289 A * | 3/1999 | Yarush et al. | 600/179 |
| 5,882,295 A | 3/1999 | Kope | |
| 5,892,630 A | 4/1999 | Broome | |
| 5,919,128 A * | 7/1999 | Fitch | 600/166 |
| 5,919,130 A | 7/1999 | Monroe et al. | |
| 5,928,137 A | 7/1999 | Green | |
| 5,941,817 A | 8/1999 | Crawford | |
| 5,947,958 A * | 9/1999 | Woodard et al. | 606/15 |
| 5,961,445 A | 10/1999 | Chikama | |
| 5,984,861 A | 11/1999 | Crowley | |
| 6,013,025 A | 1/2000 | Bonne et al. | |
| 6,059,720 A | 5/2000 | Furusawa et al. | |
| 6,086,542 A | 7/2000 | Glowa et al. | |
| 6,086,554 A | 7/2000 | Humphreys, Jr. et al. | |
| 6,152,872 A | 11/2000 | Peck et al. | |
| 6,179,776 B1 | 1/2001 | Adams et al. | |
| 6,190,353 B1 | 2/2001 | Makower et al. | |
| 6,275,255 B1 | 8/2001 | Adair et al. | |
| 6,293,910 B1 | 9/2001 | Yamakita et al. | |
| 6,306,083 B1 * | 10/2001 | Bonne et al. | 600/182 |
| 6,310,642 B1 | 10/2001 | Adair et al. | |
| 6,322,498 B1 | 11/2001 | Gravenstein et al. | |
| 6,350,231 B1 | 2/2002 | Ailinger et al. | |
| 6,387,044 B1 | 5/2002 | Tachibana et al. | |
| 6,393,431 B1 | 5/2002 | Salvati et al. | |
| 6,411,835 B1 | 6/2002 | Modell et al. | |
| 6,432,047 B1 | 8/2002 | Gust et al. | |
| 6,478,730 B1 * | 11/2002 | Bala et al. | 600/121 |
| 6,487,440 B2 | 11/2002 | Deckert et al. | |
| 6,498,884 B1 * | 12/2002 | Colvin et al. | 385/117 |
| 6,503,196 B1 | 1/2003 | Kehr et al. | |
| 6,527,704 B1 | 3/2003 | Chang et al. | |
| 6,530,881 B1 | 3/2003 | Ailinger et al. | |
| 6,549,794 B1 | 4/2003 | Nadeau, Jr. et al. | |
| 6,561,973 B1 | 5/2003 | Bala | 600/178 |
| 6,599,238 B2 | 7/2003 | Ooshima et al. | |
| 6,612,981 B2 | 9/2003 | Onishi et al. | |
| 6,659,940 B2 | 12/2003 | Adler | 600/109 |
| 6,712,757 B2 | 3/2004 | Becker et al. | |
| 6,740,030 B2 | 5/2004 | Martone et al. | |
| 6,761,684 B1 | 7/2004 | Speier | |
| 6,761,685 B2 | 7/2004 | Adams et al. | |
| 6,808,505 B2 | 10/2004 | Kadan | |
| 6,826,422 B1 | 11/2004 | Modell et al. | |
| 6,936,004 B2 | 8/2005 | Utsui | |
| 2001/0000040 A1 | 3/2001 | Adams et al. | |
| 2002/0013513 A1 | 1/2002 | Bala | |

FOREIGN PATENT DOCUMENTS

| | | |
|---|---|---|
| EP | 0 072 205 | 2/1983 |
| EP | 0 316 244 | 5/1989 |
| EP | 0 461 669 | 12/1991 |
| EP | 0461669 A1 * | 12/1991 |
| EP | 0 511 805 | 4/1992 |
| EP | 0549097 | 6/1993 |
| EP | 0 586 162 | 3/1994 |
| EP | 0 647 425 | 4/1995 |
| GB | 2 339 922 | 2/2000 |
| JP | 59-002005 | 1/1984 |
| JP | 01-204642 | 8/1989 |
| JP | 04-177310 | 6/1992 |
| JP | 05-253167 | 10/1993 |
| JP | 05-317241 | 12/1993 |
| JP | 06-202007 | 7/1994 |
| JP | 06-209904 | 8/1994 |
| JP | 06-250104 | 9/1994 |
| JP | 07-013087 | 1/1995 |
| JP | 08-110486 | 4/1996 |
| JP | 09-178446 | 7/1997 |
| JP | 2000-000203 | 1/2000 |
| JP | 00-097846 | 4/2000 |
| JP | 01/264644 | 9/2001 |
| WO | WO 92/22238 | 12/1992 |
| WO | WO 94/08505 | 4/1994 |
| WO | WO 94/14367 | 7/1994 |
| WO | WO 96/39916 | 12/1996 |
| WO | WO 97/05473 | 2/1997 |
| WO | WO 97/09937 | 3/1997 |
| WO | WO 98/20787 | 5/1998 |
| WO | WO 98/35607 | 8/1998 |
| WO | WO 99/35960 | 7/1999 |
| WO | WO 00/03272 | 1/2000 |
| WO | WO 00/13568 | 3/2000 |
| WO | WO 01/19235 | 3/2001 |
| WO | WO 01/22866 | 4/2001 |

* cited by examiner

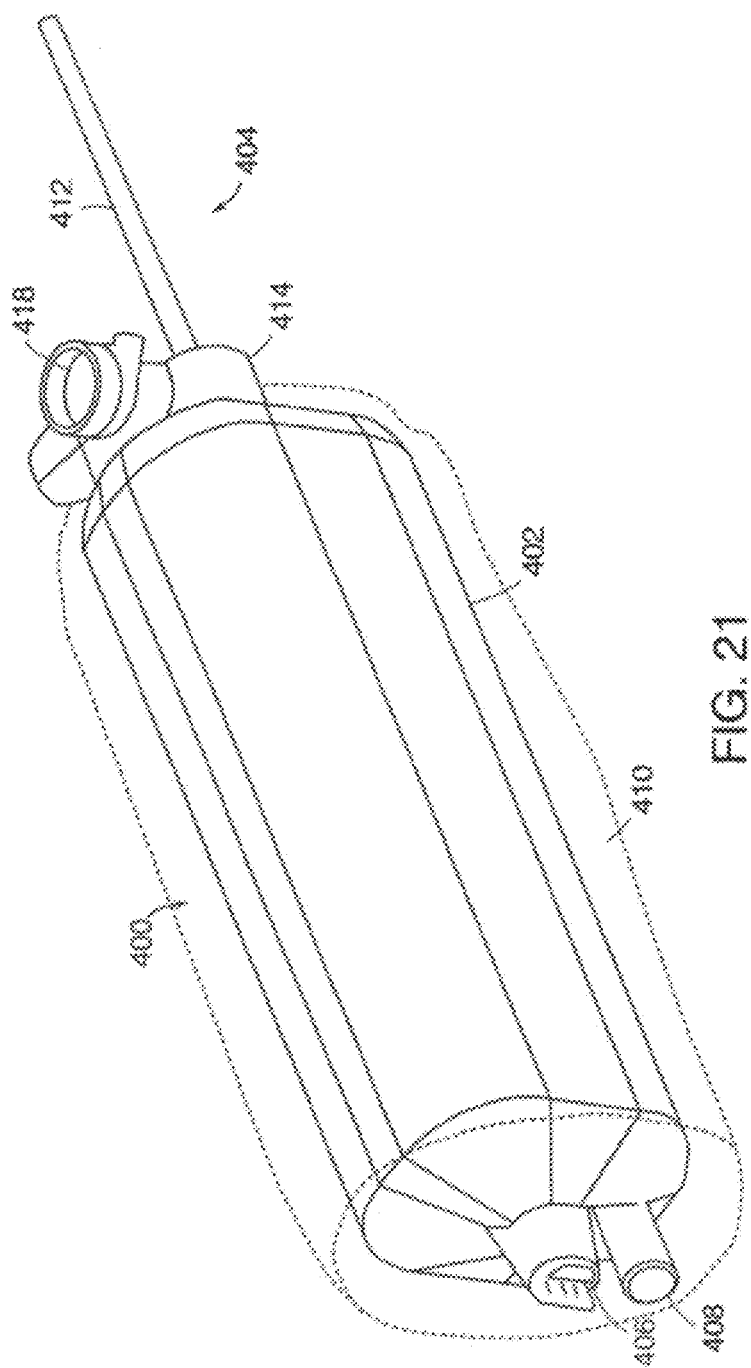

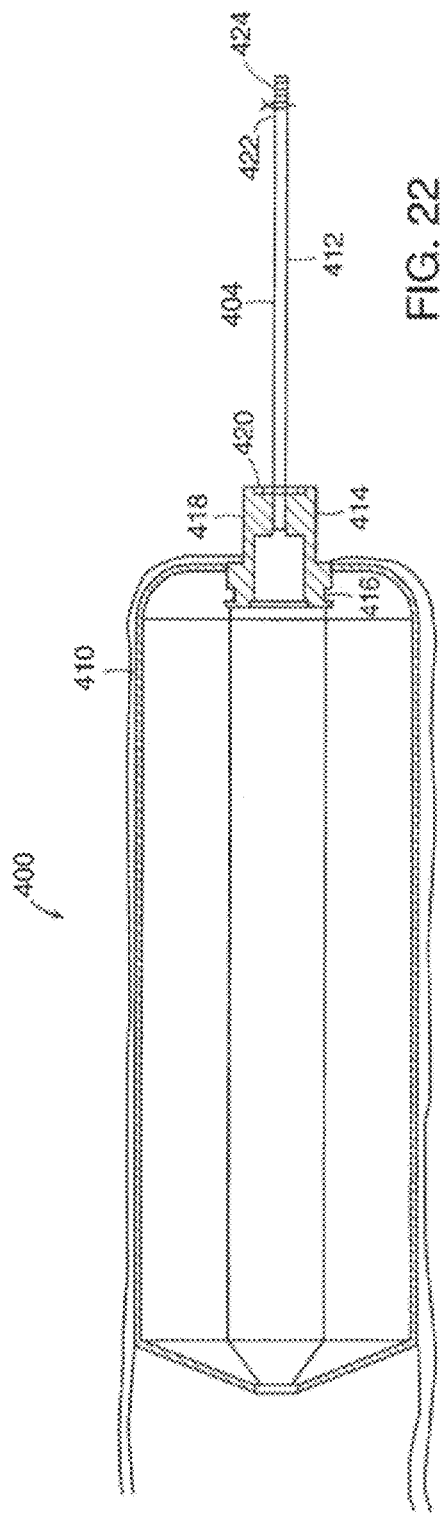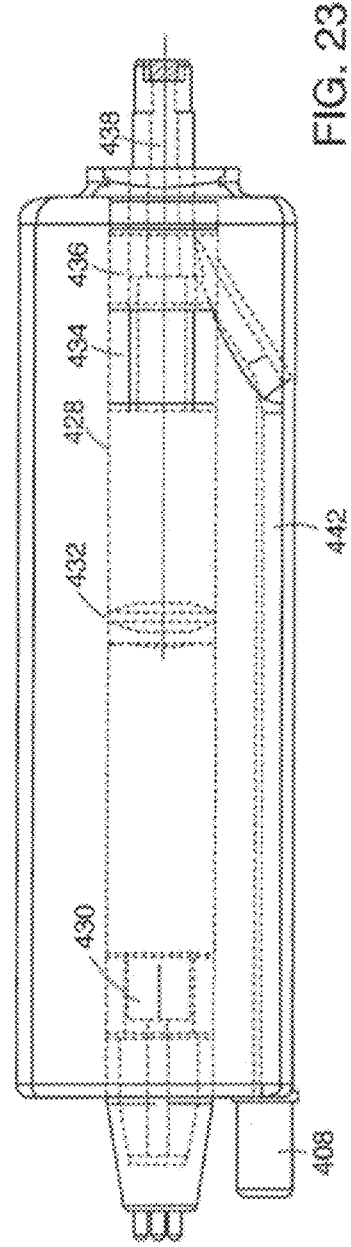

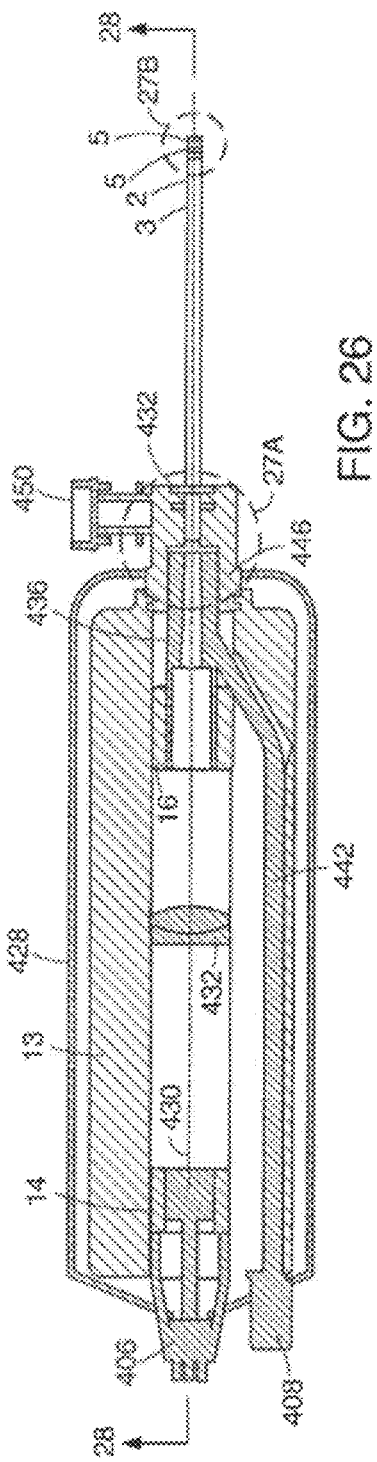
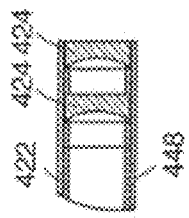
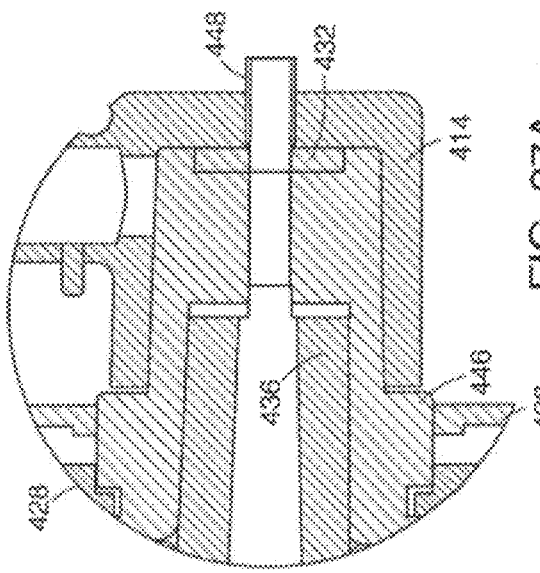

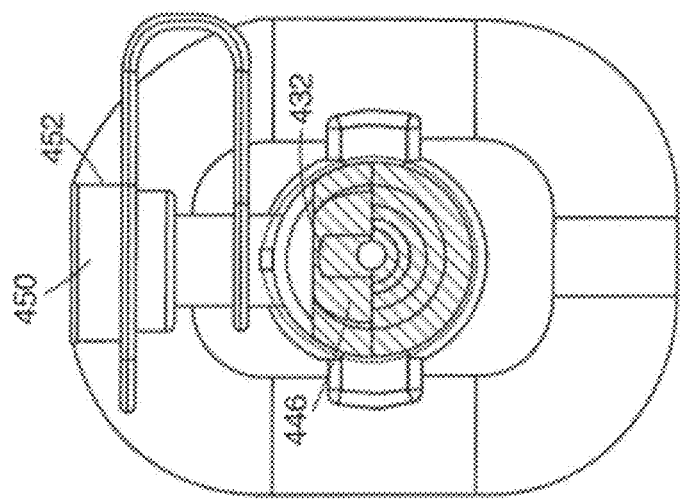
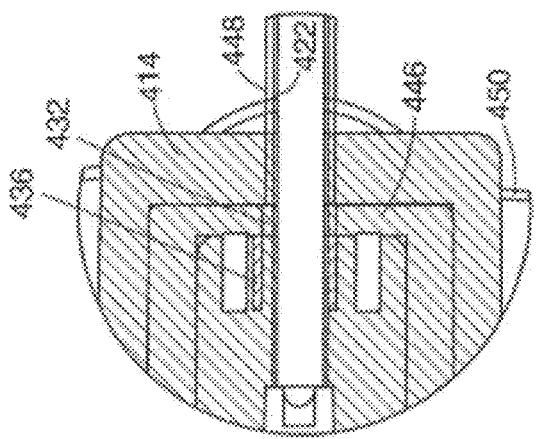
FIG. 29A
FIBER OPTIC CONNECTION TRANSMITS
LIGHT TO LIGHT-SHEATH THROUGH OPTICS HUB
WINDOW/LENS IN DISPOSABLE OPTICS TIP ASSEMBLY
FIG. 29B

MINIATURE ENDOSCOPE SYSTEM

RELATED APPLICATION

This application claims the benefit of U.S. Provisional Application Nos. 60/212,935 filed Jun. 20, 2000, 60/187,305 filed Mar. 6, 2000, 60/156,478 filed Sep. 28, 1999 and 60/153,568 filed Sep. 13, 1999 and is a Continuation-in-Part (CIP) of 09/518,954, filed Mar. 6, 2000, the teachings of which are incorporated herein by reference in their entirety. This application also relates to U.S. application Ser. No. 09/520,648 filed Mar. 6, 2000, and U.S. application Ser. No. 09/521,044, filed Mar. 6, 2000, the contents of the above applications are incorporated herein by reference in their entirety.

BACKGROUND OF THE INVENTION

Endoscopes are devices which allow visual examination inside a hollow cavity. In the field of medicine, the use of endoscopes permits inspection of organs for the purpose of diagnosis, viewing of a surgical site, sampling tissue, or facilitating the safe manipulation of other surgical instruments. Laparoscopes are used particularly for examining organs in the abdominal area. Laparoscopes typically include a light pipe for illuminating the region to be viewed, at least one lens assembly for focusing and relaying the image of the illuminated object, and a housing for the entire assembly which is structured to minimize tissue damage during the surgical procedure. The light pipe can include a fiber optic element for illuminating the site. The laparoscope housing includes a distal section that can be inserted within a body cavity and a proximal section which can include a handle that a user grips to position the distal end near the surgical site.

Existing laparoscopes can include an imaging device such as a charge coupled device (CCD). This device can capture an image of an object being viewed and convey it to a display device, such as monitor. There is a continuing need to improve on the operational features and manufacturability of endoscope systems that improve imaging capability and reduce the risk to the patient.

SUMMARY OF THE INVENTION

The present invention relates to a small diameter imaging probe or endoscope having improved resolution and field of view. The distal end of the probe, that is inserted into the tissue under examination, is preferably less than 2 mm in diameter to reduce trauma at the point of insertion and thereby provide access to sites that are otherwise unavailable for endoscopic examination.

In a preferred embodiment, the endoscope has an optical waveguide or elongated rod, which can be made of a transparent material such as a high refractive index glass, an illumination channel, an optical system and an imaging sensor. The outer diameter of the elongated rod is preferably in the range of 0.6-1.6 mm. The imaging device is optically coupled to the rod using one or more lenses.

The waveguide can be used to conduct light from a distal end to a proximal end of the device. The rod can have an outer surface which is coated with an absorbing material or light absorbing layer to inhibit internal reflection and scattering of light. One or more lenses at the distal end of the rod can provide enhanced coupling of light into the distal aperture of the rod.

The illumination channel can surround the rod and transmits light from a light source to an object being examined. The illumination channel is formed with or on the outer surface of the light absorbing layer. A dispersive element can be placed at the distal end of the illumination channel to enhance illumination of the region of interest.

The imaging device can be a charge coupled device (CCD), a CMOS imaging device or other solid state imaging sensor having a two dimensional array of pixel elements. The sensor can capture an image as an object being viewed and transmit it to a computer for storage, processing and/or a display.

In another preferred embodiment, the endoscope has an optical system which includes distal optics and an image relay or tube. The tube can have an inner channel such as a hollow cylinder coated with a light absorbing material to inhibit internal reflection and scattering of light. The endoscope has a duplex configuration which uses a beamsplitter to direct illumination light along the same optical path or air tube used for the transfer of image light from an object being imaged.

The system can use a sheath assembly to provide a sterile barrier over the handle. The barrier can be disposable along with the needle probe.

The light source can be a high power light source. The light can be concentrated by source optics to a polarizer and to a beam splitter before traveling through the tube. The illumination light can be polarized to improve delivery and collection efficiency.

The miniature endoscope system can be used for orthopedic, rheumatologic, general laparoscopic, gynecological or ear, nose and throat procedures, for example. Although many applications require a small diameter to reduce trauma, certain applications can accommodate larger diameters.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 21 is a perspective view of an alternative embodiment of the miniature endoscope;

FIG. 22 is a top sectional view of the miniature endoscope;

FIG. 23 is a side view, a portion shown in hemline of the miniature endoscope;

FIG. 26 is a side sectional view of the miniature endoscope;

FIG. 27A is an enlarged sectional view of a portion of the endoscope of FIG. 26;

FIG. 27B is an enlarged sectional view of the distal end of the endoscope of FIG. 26;

FIG. 29A is an enlarged sectional view of a portion of the endoscope of FIG. 28;

FIG. 29B is an enlarged sectional view of a portion of the endoscope of FIG. 28.

DETAILED DESCRIPTION OF THE INVENTION

Figure 1:
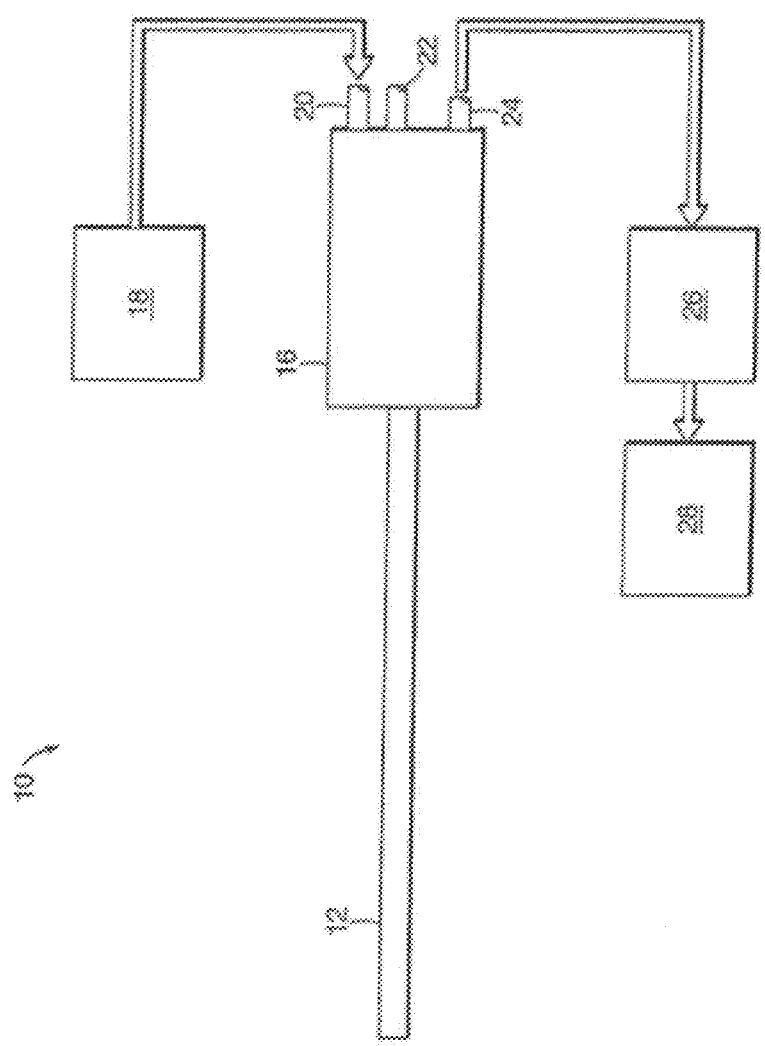
FIG. 1 illustrates a schematic illustration of a preferred embodiment of the endoscope.

A preferred embodiment of the invention is illustrated in FIG. 1 which shows a miniature endoscope 10. The endoscope 10 has an image transmission path such as an optical waveguide or elongated rod 12 used to view objects to be examined. The elongated rod 12 can be attached to a handle 16. The handle 16 can house a light source input 20 which can connect to a light source 18. In a preferred embodiment, the light source input 20 such as a fiber optic cable optically couples the light source 18 to an illumination channel within the endoscope 10. The handle 16 can also house a power input 22, used to provide power to the endoscope 10. Alternatively, the light source and/or power source can be mounted within the handle.

The handle 16 can also house an image output 24. The image output 24 provides a connection between an imaging device in the endoscope and an electronic storage and/or display device. In one embodiment, the storage device is a computer 26 which is connected to a monitor 28. The imaging device can be a charge coupled device or other pixellated flat panel sensor.

Figure 2:
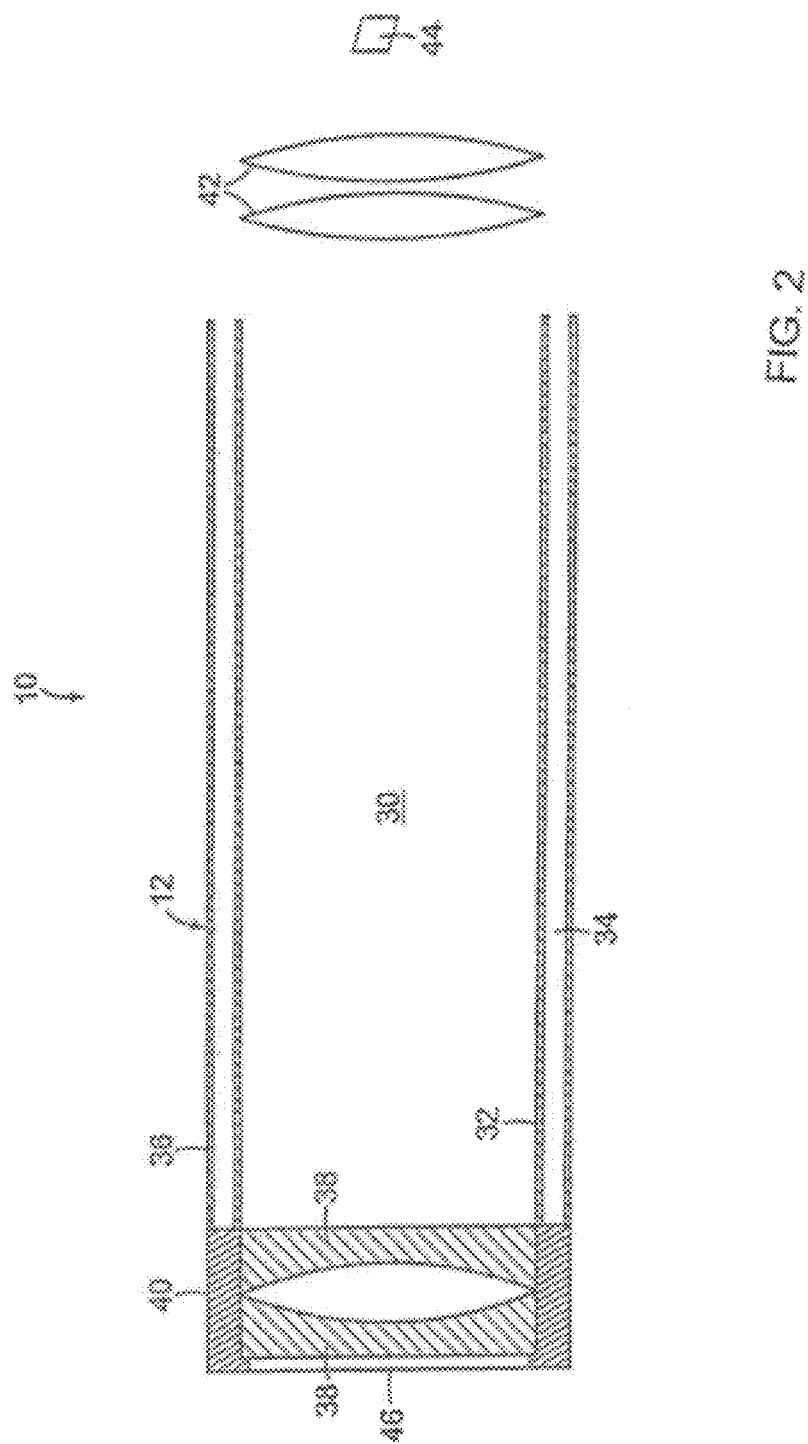
FIG. 2 shows a cross-sectional view of the endoscope optical system.

FIG. 2 shows a cross-sectional view of an embodiment of the microendoscope 10. The elongated rod 12 can have a transparent material such as a high index glass rod 30 having a refractive index greater than one, an illumination channel 34, an optical element or distal optics 38 and proximal optics 42.

The distal optics 38 can form a virtual image of an object being examined. In a preferred embodiment, the distal optics 38 can be one or more plastic lenses. The high index glass rod or core 30 links the distal optics 38 to relay optics 42 located in a proximal end of the endoscope 10. In one embodiment, the distal optics comprise two lenses. The high index glass core 30 can have a refractive index of 1.85 and can reduce the optical path between a virtual image created by the distal optics 38 and the relay optics 42. The high index glass rod 30 is preferably free of birefringence to produce an aberration free image at an image sensor 44. Stress within the glass core 30 is necessary for mechanical strength. In a preferred embodiment, the glass core 30 is made of SF57, a pochels glass, which is a glass that can be mechanically stressed without introducing stress birefringence.

The high index glass core 30 can have a tunnel barrier or light absorbing layer or sheath 32. The purpose of the tunnel barrier or sheath 32 is to absorb unwanted light. One option for a tunnel barrier is described in U.S. Pat. No. 5,423,312, the entirety of which is incorporated herein by reference. This option employs a glass rod having an outer surface that has been roughened and blackened to provide an absorbing barrier. In contrast, the present invention leaves the glass rod intact and provides an external coating having a lower index of refraction to absorb light crossing the rod's external surface. In a preferred embodiment, the tunnel barrier or absorbing sheath 32 is EMA or extramural absorption glass (available from Shott Fiber Optics, Southbridge, Mass.). The EMA glass can be extruded during a fiber optics drawing process. The extrusion process leaves the outer surface of the high index glass rod intact. The extruding process instead adds material to the outer surface of the high index glass rod 30 to create a reflective boundary. The extruding process can be performed using a bar in tube drawing process. Similarly, the extruding process can be performed using a differential bar in tube drawing process. In a preferred embodiment, the EMA glass is approximately 5-10 µm thick. The EMA glass can have a refractive index of 1.6, for example.

The illumination channel 34 can be used to provide light from a light source to an object being illuminated. In one embodiment the illumination channel is coupled to glass fiber which is coupled to a light source. In a preferred embodiment, the illumination channel 34 can be extruded during a fiber optics drawings process. In another embodiment, this fiber optic drawing process can be performed in a second drawing process. The illumination channel can have a wall thickness of 0.15 mm and can have a refractive index of 1.5 for example. Generally, the illumination channel has a wall thickness in a range of 0.1 mm and 0.2 mm.

The image channel or illumination channel 34 can have an outer sheath 36. In a preferred embodiment, the outer sheath 36 is a polyamide coating. The coating can be between 100 and 150 µm thick. The polyamide coating can be applied in a final fiber optics drawing process. Alternatively, one or more of the layers on the rod can be applied by a coating, dipping or deposition process. The polyamide coating can provide strength to the glass core 30. If a glass shatter event were to occur, the polyamide coating can contain the glass from the core 30 to prevent injury to the patient. An outer metal or plastic tube can also be used to enclose the distal end of the device.

The elongated rod 12 can also have a binary phase ring 40 located at its distal end. The ring 40 is positioned on the elongated rod 12 so as to abut the illumination channel 40. The binary phase ring is coupled to the illumination channel in one embodiment. The binary phase ring 40 disperses light traveling through the illumination channel 34 to provide even illumination of the field of view. In a preferred embodiment, the binary phase ring 40 is made from a plastic material. The binary phase ring 40 can also have a distal window 46. The window can be mounted flush against the distal optics 38.

The elongated rod 12 of the endoscope 10 in one embodiment has an outer diameter under 2 mm. In another embodiment, the endoscope 10 has an outer diameter of 1.6 mm or less. In a preferred embodiment requiring a small entry site, the endoscope 10 has an outer diameter of 1 to 1.2 mm.

Figure 3:
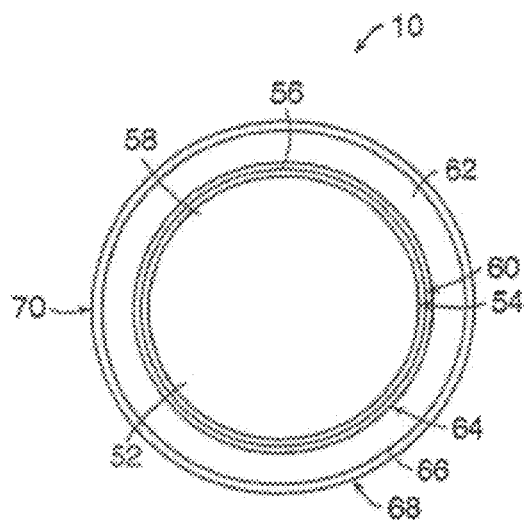
FIG. 3 illustrates a front view of an embodiment of the endoscope optical system.

FIG. 3 illustrates a front view of an embodiment of an endoscope 10. The endoscope 10 can have an image light channel 58 and a super-clad structure 68. The image light channel 58 can include and a light absorbing layer 56. The super-clad structure 68 can include a first coating or layer 64, a second coating or layer 66 and an illumination channel 62. The super clad structure 68 directs light through the endoscope 10.

The image light channel 58 can be made from a transparent material or high index glass core 52. In a preferred embodiment, the core 52 is made from a material having a constant refractive index to eliminate deviation of light passing through the material. The constant refractive index may be achieved after the stress of a fiber drawing process by using a pockels glass core, for example. Pockels glasses exhibit zero birefringence when placed in compression or tension. The constant refractive index may also be achieved by annealing the image light channel 58 after the fiber drawing process. The core 52 can also have a first diameter 54. In a preferred embodiment, the first diameter 54 is 1.20 mm.

The light absorbing layer 56 of the image light channel 58, in a preferred embodiment, is a light absorbing glass. The light absorbing layer 56 can have a higher index of refraction than the core 52 and can be made from the same material as the core 52. Light absorbing colorants can be added to the light absorbing glass material to raise its index of refraction and increase its light absorption. In a preferred embodiment, the index of refraction of the light absorbing layer 56 is slightly higher than the index of refraction of the core 52. The light absorbing layer 56 can be applied to the core 52 using a fiber drawing process, for example.

The high index glass core 52 and light absorbing layer 56 can be formed from various types of glass materials. In one embodiment, the image light channel 58 can be formed from an F2 glass core and a BG-4 glass light absorbing layer. The F2 glass core can have a refractive index of 1.620. The BG-4 glass light absorbing layer can have a refractive index of approximately 1.65. In another embodiment, the image light channel 58 can be formed from an F7 glass core and a BG-2 glass light absorbing layer. The F7 glass core can have a refractive index of 1.625. The BG-2 glass light absorbing layer can have a refractive index of approximately 1.66.

The light absorbing layer 56 can have a thickness as low as 5 µm. Preferably, the thickness of the light absorbing layer 56 is no greater than 10 µm. The image light channel 58, formed of the core 52 and the light absorbing layer 56, can have a second diameter 60. In one embodiment, the second diameter 60 is 1.24 mm.

The illumination channel 62 has the first coating 64 and the second coating 66 to form a super-clad structure 68. The first coating 64 is located on an inner surface of the channel 62. The second coating 66 is located on an outer surface of the channel 62. The illumination channel 62 can be made from a high index of refraction material. In one embodiment, the illumination channel 62 can be made from LG1 glass which can have a refractive index of approximately 1.82. Both the first coating 64 and the second coating 66 can be made from a low index of refraction material. In one embodiment, the coatings 64, 66 can be made from EG1 glass which can have a refractive index of approximately 1.50. In another embodiment, the coatings can be made from EG9 glass which can have a refractive index of approximately 1.56. The low index material can provide for illumination containment of the illumination channel 62. The illumination channel 62 can have a thickness of 30 µm. The first 64 and second 66 coating layers can each have a thickness as low as 5 µm respectively. Preferably, the thickness of each of the first 64 and second 66 coating layers is 10 µm.

The super-clad structure 68 can be made by different processes such as a triple-glass, a tube-extrusion process, a dip coating process or chemical deposition combined with fiber drawing processes, for example.

In one embodiment of a process to fabricate a super-clad structure 68, the image light channel 58 can be exposed to a triple-glass tube-extrusion process, which can form the super-clad structure 68. A bar-in-tube fiber draw can then be used to fuse the super-clad structure 68 around the image light channel 58.

In another embodiment of forming a super-clad structure 68, an image light channel 58 can be dipped in a low index, high temperature polymer to form a first coating 64. A high index plastic can then be extruded over the polymer clad image light channel 58, to form an illumination channel 62. The entire structure can then be dipped in a low index polymer to form the second coating 66.

In another embodiment of a process of fabricating a super-clad structure 68, a metal layer can be chemically deposited onto both sides of an illumination channel 62 to form a super-clad structure 68. In a preferred embodiment, the metal is aluminum. The super-clad structure 68 can then be fused to an image light channel 58 using a bar-in-tube fiber drawing process. The super-clad structure 68 and the image light channel 58, the endoscope 50 can have a third diameter 70. In one embodiment, the third diameter 70 is 1.65 mm.

Figure 4:
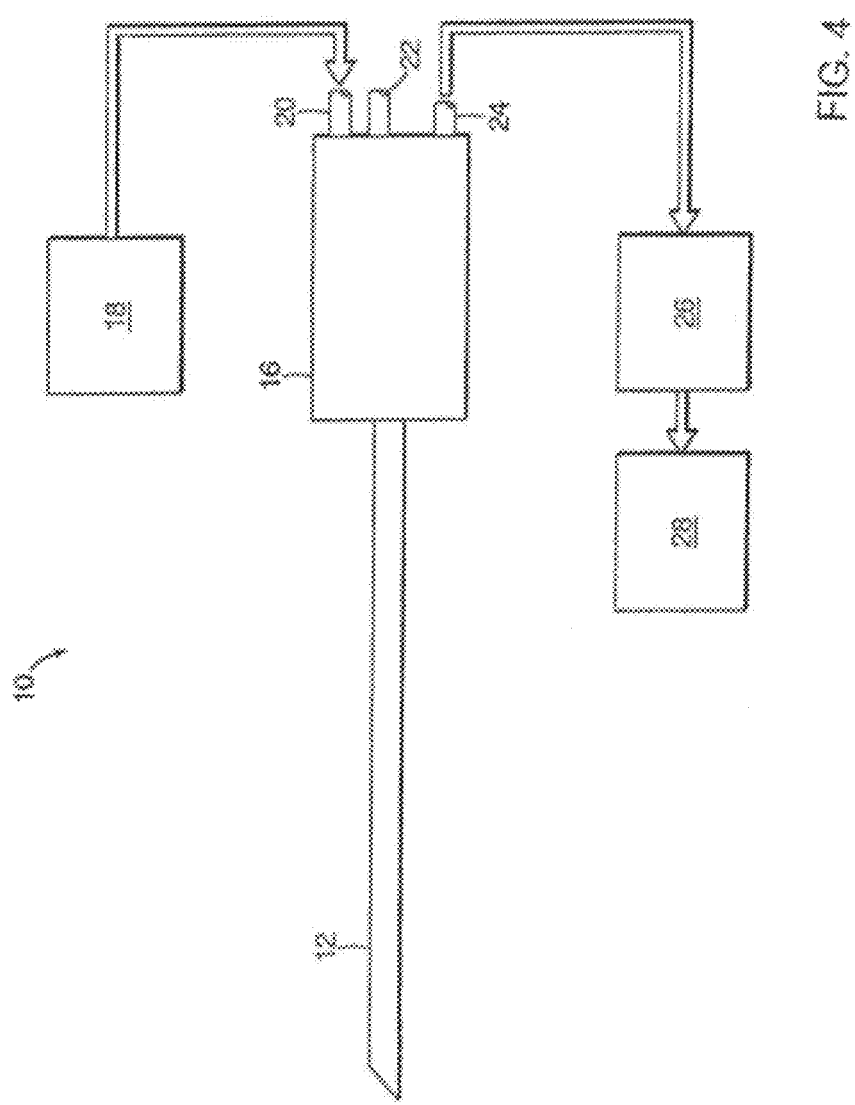
FIG. 4 shows a schematic illustration of an alternate embodiment of the endoscope shown in FIG. 1.

In an alternate embodiment, the endoscope can have an angled distal tip in the shape of a needle shown in FIG. 4. This tip provides for ease of insertion at the site to be examined.

The endoscope can also have square or rectangularly shaped distal optics which can form a virtual image of an object being examined. The endoscope can also have an image transmission path or image channel, such as an elongated rod, which can have a square or rectangularly shaped cross section. Similarly, the endoscope can have square or rectangularly shaped relay optics. By using rectangular optics or a rectangular transmission path, a more efficient transfer of light can be made from an object being viewed to an imaging device, which has a square or rectangular imaging area. All light from an object being imaged can be directly transferred to the imaging area, with little to no light wasted during the transfer.

Generally, endoscopes have circular optics which can transmit light rays to a rectangularly shaped imaging device. For endoscopes having optics with circular cross-sectional areas greater than the cross-sectional area of the imaging device, a portion of the light rays traveling in the arcuate areas of the circular optics will not be transmitted to the imaging device. These light rays can be considered as "wasted" since the light rays fail to intersect the imaging device and are, therefore, unused.

Figure 5:
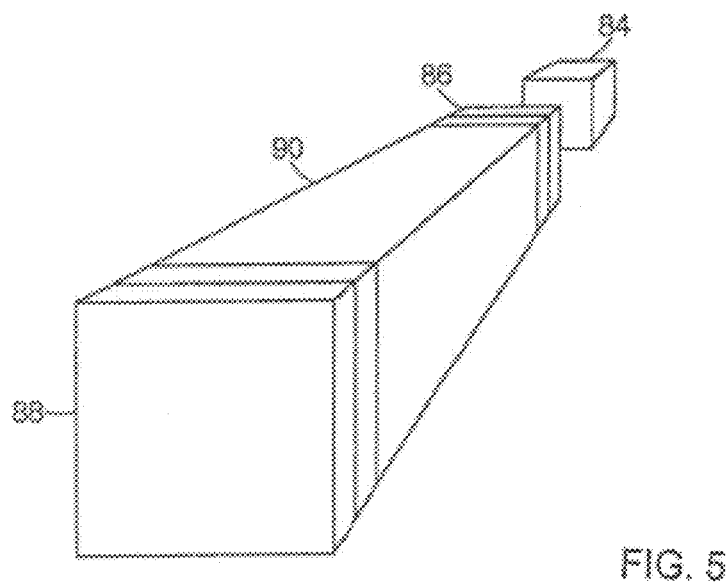
FIG. 5 illustrates rectangular optics and a rectangular image transmission rod of an endoscope transmitting light to an imaging device.

FIG. 5 illustrates rectangular distal optics or optical elements 88 for an endoscope which can transmit light rays to an imaging device 44. In this embodiment, all light rays from the rectangular distal optics 88 can be transferred to the imaging device 84. More light from the object being imaged can therefore be transferred to the imaging device 84 with little waste. A rectangularly shaped transmission path 90 can be used to transfer the light from the distal optics 88 to the imaging device 44. Rectangularly shaped relay optics 86 can also be used to transfer the light from the distal optics 88 to the imaging device 44.

Figure 6:
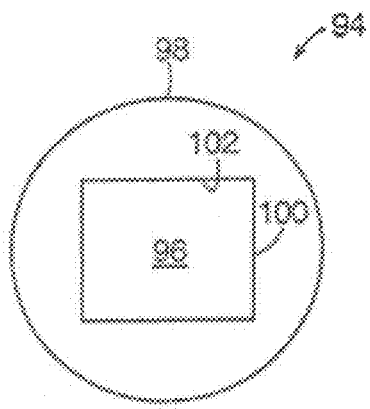
FIG. 6 illustrates a super-clad structure integrated over a square or rectangular transmission path of an endoscope.

When a square or rectangular transmission path is used in a microendoscope, the inner surface of a super-clad layer of the microendoscope can be shaped to conform to the outer surface of the transmission path. FIG. 6 illustrates a microendoscope 94 having a rectangular light transmission path 96 and a super-clad layer 98. The light transmission path 96 has an outer surface 100 which can be coated with a light absorbing layer which conforms to the geometry of the outer surface 100. When the super-clad layer 98 is to be applied to or extruded over the light transmission path 96, an inner surface 102 of the super-clad layer 98 can conform to the geometry of the light transmission path 96, as illustrated. For a square light transmission path 96, the inner surface 102 of the super-clad layer 98 can be extruded square over the transmission path 96.

Figure 7:
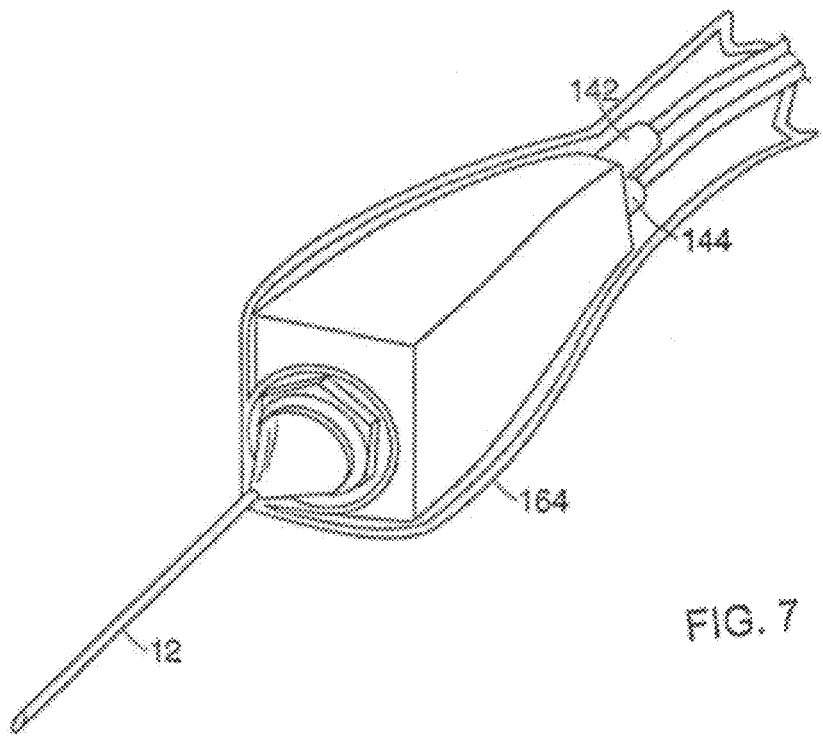
FIG. 7 illustrates a perspective view of a preferred embodiment of the invention.

FIG. 7 shows a perspective view of a miniature needle endoscope in accordance with the invention. Fiber and electrical cables are connected to the proximal end of handle 16 or needle 12 for insertion into a patient is attached at a distal end of handle 16.

Figure 9:
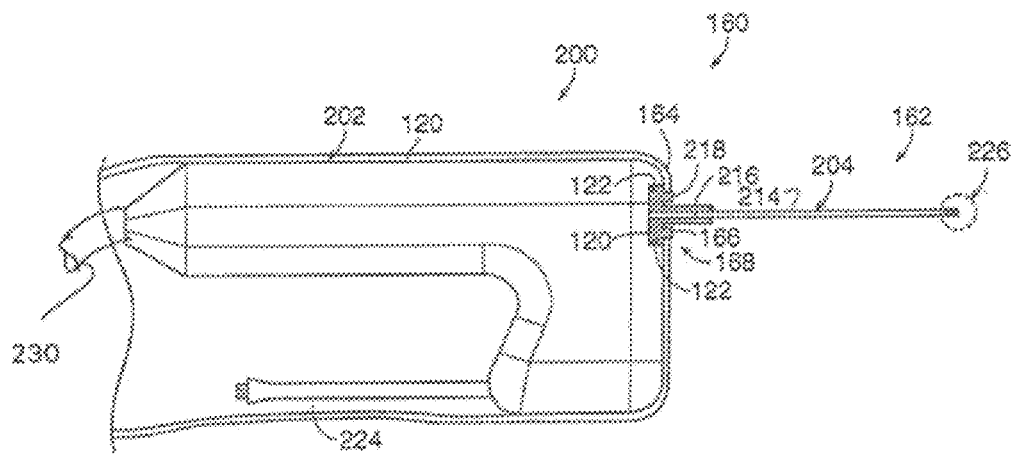
FIGS. 9 and 10 show a side view and a perspective view, respectively, of a miniature endoscope.
Figure 19:
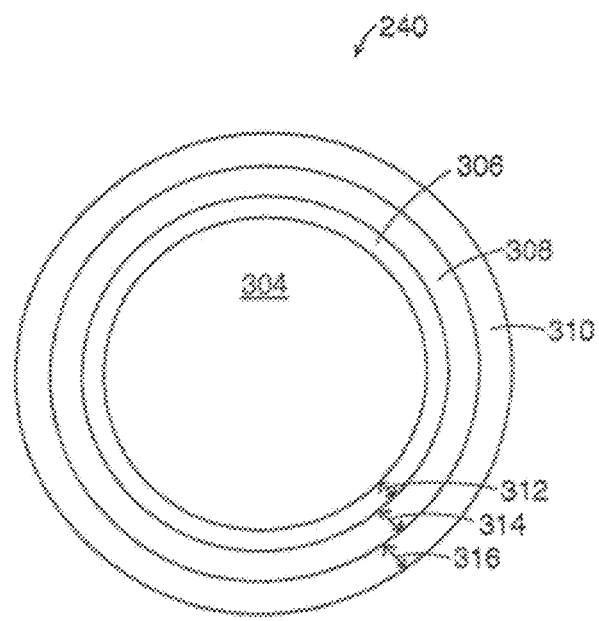
FIG. 19 illustrates a cannula for a miniature endoscope; the cannula having an illumination cannula.

A preferred embodiment of the invention can be considered as three subassemblies. A first subassembly shown in FIG. 9 is the outer handle housing 120 having a distal rod connector 122. A second subassembly is the inner handle 140 shown in FIG. 12. Inner handle 140 includes proximally located fiber and electrical connectors 142 and 144 that are attached to an inner cage assembly 146. The fiber connector 142 connects light from an external source to an illumination annulus 154 which couples light to an illumination channel 308 in needle 240 as shown in FIG. 19. Light collected through needle 240 is coupled to lenses 150 and 152 onto an imaging sensor such as CCD 148.

FIGS. 9 and 12-14 illustrate a disposable third assembly having a rod and needle with a distal lens assembly 162 that is attached to a sterile sleeve assembly 160. The sleeve assembly 160 includes a sleeve 164 that extends over the handle or base unit 202. The distal end of sleeve 164 is secured between plastic frames 166, 170 which can form a mounting hub 218. Frame 166 has a hole 168 that connects to rod and lens assembly 162. Frame 170 connects to rod connector or interface connector 122.

Figure 8:
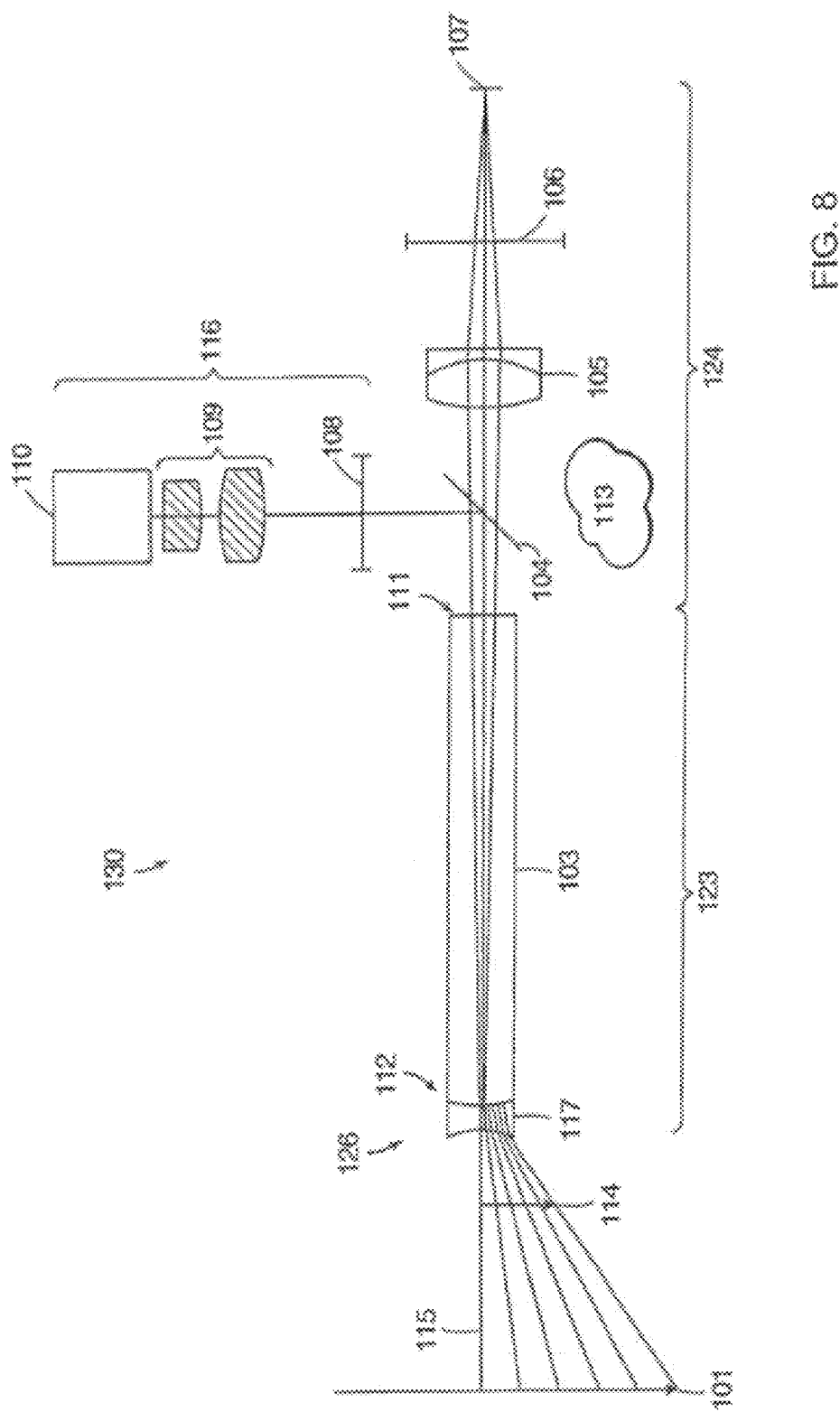
FIG. 8 illustrates an endoscope having an air tube and a duplex configuration.

FIG. 8 illustrates an endoscope, identified generally as 130. The endoscope 130 can have an optical system 123 and a handle 124. The optical system 123 can include a tube 103 having a distal end 112, a proximal end 111 and distal optics 117 and can have an outer diameter between 0.6 and 2.0 mm with a preferred outer diameter of about 1.6 mm. The optical system 123 can be disposable. The handle portion 124 can include proximal optics 105, an image polarizer 106, an image sensor 107 and a beam splitter 104. The proximal optics 105 can include an achromatic lens. The beam splitter 104 can be coated with a dielectric coating. The beam splitter coating can be designed to provide maximum reflection of "s polarized" illumination flux and maximum transmission of "p polarized" image light. The curvature of the distal optics 117 can be chosen to minimize retro-reflections of illumination flux appearing in the image.

The endoscope 130 can have a duplex configuration wherein the duplex configuration integrates illumination optics and uses the beam splitter 104 to direct illumination energy along the same optical path used for image light transfer. "Duplex" refers to the optical components and optical path used by illumination flux and image light.

The basic optical components used for both the image light and illumination flux in the endoscope 130 are shown in FIG. 8. As part of the imaging component of the endoscope 130, an object plane 101 can be located from 2 to 20 mm in front of a distal tip 126 of the endoscope 130. The distal optics 117 form a demagnified virtual image 114, located just outside the distal tip 126. A narrow beam of image light from the virtual image 114 can pass through the tube 103, through a dielectric coated beam splitter 104, toward proximal optics 105, and eventually to an image sensor 107, where a real image is formed. Image polarizer 106 can be a linear polarizer that is "crossed" with an illumination polarizer 108 to block retro-reflected illumination flux originating from surfaces of the distal optics.

The tube 103 can be a stainless steel extrusion having a rough inner surface which can be coated with a light absorbing coating, such as spray paint. For example, Krylon #1602, a dull black paint can be used. The tube 103 can have an inner diameter of 1.5 mm with the light absorbing inner wall to reduce or eliminate veiling or scattered light at the image sensor 107. The tube 103 can be filled with air or some other inert gas, or can be evacuated.

The image channel or image relay 103 functions to minimize or absorb unwanted light and hard to image light to prevent veiling glare. The image relay 103 provides high resolution of the optical image, 114 at the plane of the imaging device, removes intermediate image planes and reduces the tolerances needed for optical alignment and optical fabrication. The image relay 103 has an inner tunnel wall that can absorb light diverging from the optics 117. The rough wall surface can disperse up to about 95% or more of unwanted light. The image relay 103 can have a length to diameter (L to D) ratio of between 40:1 and 60:1. The length of the tunnel can be approximately 60 mm. The length of the image relay 103 affects proper illumination of an imaging device, helps control depth of field of view, increases F number for adequate depth of field of view. The image relay 103 can also be disposable.

The optical element or distal optics 117 on the tube 103 can be a polymer lens or an epoxy lens. The distal optics can have a diameter of 1.5 mm. The distal optics 117 can be a single distal lens to reduce retro-reflections. The distal optics 117 can be formed from an epoxy using an injection method. In this method a mandrel can first be placed within the tube 103 from the distal end 112 to the proximal end 111. Epoxy can then be ejected from the needle within 1 mm of the distal end 112 of the tube 103. The epoxy can then be exposed to ultraviolet (UV) light to cure the epoxy. The distal optics 117 can be formed as a concave/negative lens because of the capillary action caused by the air tube 103 after ejection of the epoxy from the needle. The distal 117 and proximal 105 optics can allow control of the size of an image.

The area surrounding the proximal end 111 of the tube can be carefully sculpted and blackened to reduce retro-reflected energy at the image sensor 107 originating from the illumination flux overfill of the air tube 103. The proximal optics 105 are "looking at" this overfill area and the image polarizer 106 can transmit scattered, unpolarized light to the image sensor 107.

The endoscope 130 can be linked via 'beamsplitter 104 to an illumination system 116. The illumination system 116 can include an illumination source 110 such as a COTS lens end Halogen Lamp having a 0.25 inch diameter from Gilway Technical Lamp. The COTS "Lens End" lamp can have high flux output from a small filament. The illumination source 110 can provide high color temperature visible light for object plane 101 illumination. Source optics 109 can concentrate illumination flux at the proximal end 111 of the tube 103 and provide a low divergence beam to maximize transmission of illumination flux through the tube 103. A beam splitter 104 can redirect illumination flux along an image light axis 115. Illumination polarizer 108 is a linear polarizer oriented to provide "s polarization" at the beam splitter to maximize reflection of illumination flux from dielectric coated beam splitter 104, along axis 115. A light absorbing mechanism or beam dump 113 can remove unused portion of illumination flux from the system to reduce veiling background light that can find its way onto the image sensor.

Illumination optics must be carefully designed to maximize illumination at object plane. The illumination optics create a small spot of light at proximal end of air tube and a collimated beam for maximum transmission through air tube.

Illumination and image polarizers must provide high polarization purity with minimum absorption. For example, dichroic sheet polarizers can be inexpensive, but lossy. Calcite polarizers can be more efficient, but expensive and more difficult to accommodate in a simple optical design.

Unused illumination flux transmitted by the beam splitter must be completely removed from the system because the proximal optics are "looking at" the dump area 113. The image polarizer will transmit scattered, unpolarized light to the image sensor.

All retro-reflections can be minimized using well known "optical isolation" configurations, but not totally eliminated. Therefore, electronic image processing may be required to produce an acceptable image. Since the retro-reflection pattern at the image sensor is unique for each scope, this unwanted light distribution can be recorded for each scope, stored in an image buffer, and subtracted from the video image in real time.

The endoscope 130 can be inserted into a body using a cannula. During an insertion procedure, a cannula can first be inserted into a site within a body. The optical system 123 of the endoscope 130 can then be inserted within the cannula which can have an outer diameter of 1.6 mm. The optical system 123 can pass through the cannula and into the body to provide the user with an image of the site.

The system can be used with a disposable sleeve or sheath to aid in maintaining a sterile environment and reduce the sterilization requirements prior to reuse.

Figure 10:
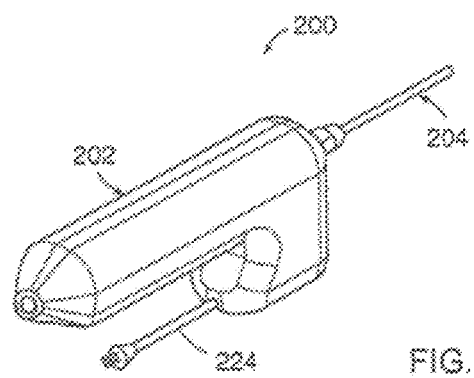

FIGS. 9 and 10 illustrate a miniature endoscope, given generally as 200, in both a side and a perspective view respectively. The endoscope 200 can include a base unit 202 and a sheath assembly 160. The base unit can include a cable 224 which can provide power to an internal light source within the base unit 202. The sheath assembly can include a sterile barrier 164 and a probe or rod and lens assembly 162. The rod and lens assembly 162 can be formed of a rod or waveguide 204 and a object lenses 206. The waveguide can be a hollow channel. The probe can have an annular illumination channel around the waveguide. The probe can have a length between 2 cm and 10 cm. The sterile barrier 164 and the rod and lens assembly 162 can be attached to a mounting hub 218 or second locking element which secures to a first locking element of the base unit 202 of the endoscope 200. The hub 218 can include an interface connection 122 or first locking element that allows the sheath assembly 160 to attach to the base unit 202. The interface connection 122 can be a securing mechanism such as a locking mechanism. The sterile barrier 164 can attach to the mounting hub 218 by bonding. The bonding can include cementing between the sterile barrier 164 and the hub 218, for example. The mounting hub 218 can include a locking mechanism 216 such as a luer lock for example. The locking mechanism 216 can allow connection between the miniature endoscope 200 and a needle such as a 14 gage cannula, for example (manufactured by Popper).

Figure 11:
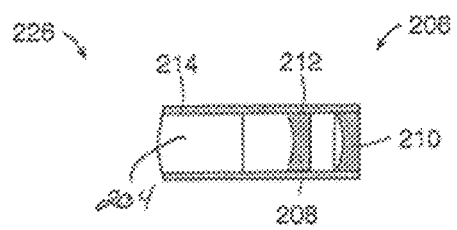
FIG. 11 illustrates a rod tip of a miniature endoscope.

The rod and lens assembly 162 can include a rod tip 226 illustrated in FIG. 11. The rod tip 226 can have object lenses 206. These object lenses can include a first object lens 208 and a second object lens 210. The rod 204 of the rod and lens assembly 162 can be covered by a tube 214 or light absorbing boundary. The tube can be a dark coating in order to reduce or eliminate veiling or scattered light within the rod 204.

The sterile barrier 164 of the sheath assembly 160 can cover the entire base unit 202. This covering provides a sterility of the base unit 202 during a surgical procedure.

Figure 20:
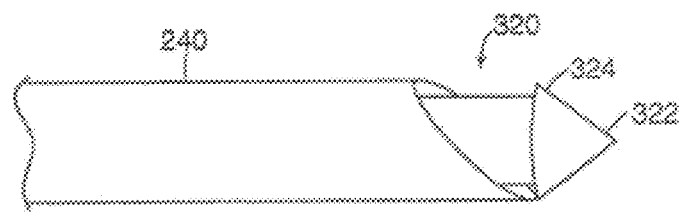
FIG. 20 shows a cannula having a stylet.

The miniature endoscope 200 can be inserted into a cannula or needle 240 as illustrated in FIGS. 12-16. Preferably the needle 240 has a blunt end. The needle can be a 14 gauge needle. To use the miniature endoscope 200 with the needle 26 in a surgical procedure, a sheath assembly 160 can first be placed on a base unit 202. The rod and lens assembly 162 of the sheath assembly 160 can lock into the interface connection 122 of the base unit 202. A needle or cannula 240, having a stylet 320, such as seen in FIG. 20, slidably mounted within the cannula, can be inserted into a surgical site. In the case where a blunt needle or cannula 240 is used, the stylet 320 can cut into the tissue of a surgical site and thereby allow the needle 240 to be inserted into the surgical site. The stylet 320 can then be removed from the cannula 240. The stylet or obturator 320 fills the center portion of the cannula during insertion into a surgical site. The use of the stylet prevents coring of tissue, whereby a cylindrical portion of tissue enters the needle or cannula 240 and can clog the needle cavity. By having a stylet within the needle 240, no such tissue can enter the cannula 240 and can clog the needle cavity.

Once the stylet has been removed from the needle 240, the user can flush the surgical site with saline. Next, the rod and lens assembly 162 of the miniature endoscope 200 can be introduced into the needle 240. The rod portion 204 can be inserted within the needle 240 so that a user can obtain a view of the surgical site. The needle can include a locking mechanism on its proximal end, such as a luer lock for example. The luer lock can attach to the locking mechanism 216 of the mounting hub 218 thereby providing a secure attachment between the endoscope 200 and the needle 240.

Figure 12:
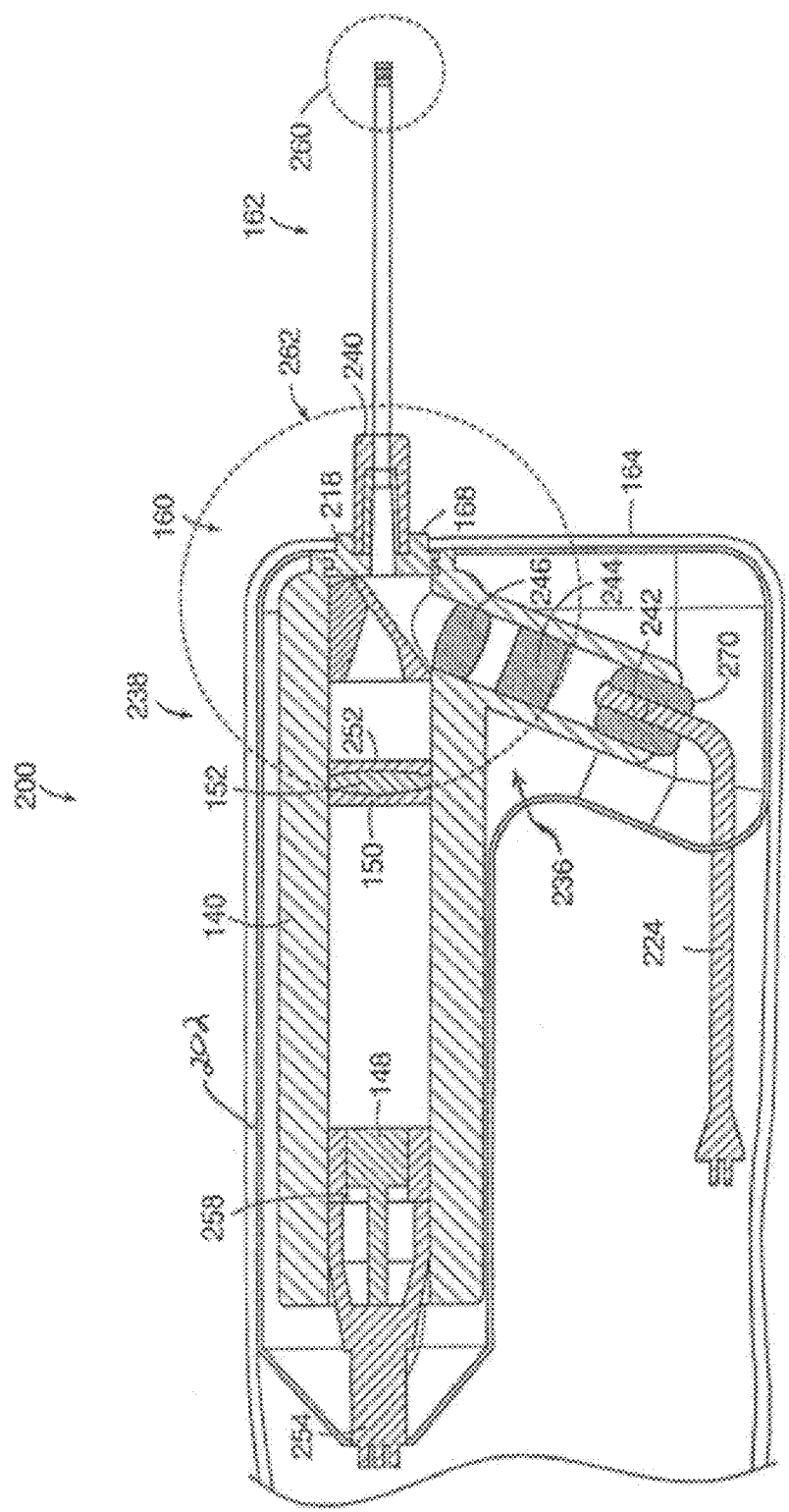
FIG. 12 shows a cross-sectional view of a miniature endoscope.
Figure 13:
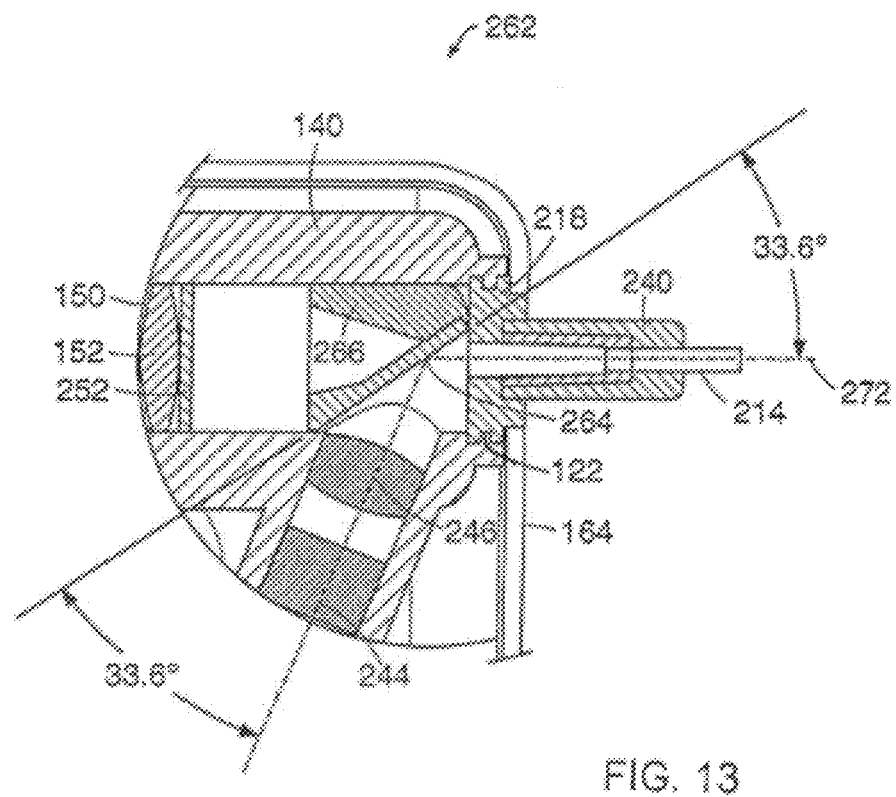
FIG. 13 shows a detailed view of the light transfer and imaging system of the endoscope of FIG. 12.
Figure 14:
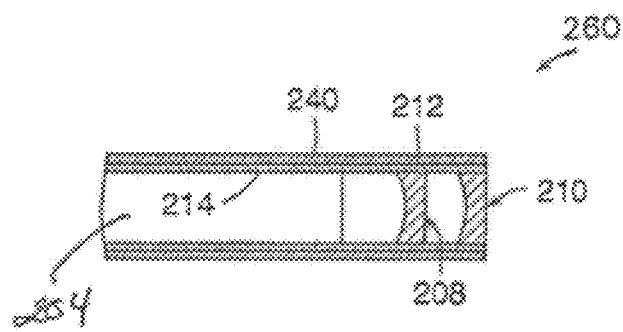
FIG. 14 illustrates a rod tip of an endoscope mounted within a needle.

FIGS. 12, 13 and 14 illustrate a cross sectional view of the miniature endoscope 200. The endoscope 200 can include a lighting system or light source 236 and an imaging system 238. The lighting system 236 can include a lamp 242, a polarizer 244 and a lens expander 246. The lamp 242 can be mounted within the base unit 202 by a light source housing 270 and can be a high output light source. The polarizer 244 can polarize light from the light source and direct light towards the expander 246. The lens expander 246 can direct light towards a prism 264.

The imaging system 238 of the endoscope 200 can include a first image path lens 150, a second image path lens 152 and a sheet polarizer 252. The imaging system can be mounted within a housing 140. The sheet polarizer 252 can help to eliminate back reflections from the rod and lens assembly 162. The polarizer 252 can have a polarization purity of $10^{-3}$.

FIG. 13 illustrates a light transfer and imaging system 262 of the endoscope 200 of FIG. 12. The light transfer and imaging system 262 can include a beamsplitter 264 which can be mounted within a housing 266 in the endoscope 200. The beamsplitter 264 can be a prism for example. The beamsplitter 266 can direct light from the lens expander 246 into the rod 204 of the rod and lens assembly 162. This light can be directed at an object to be imaged. The beamsplitter 264 can also receive image light through the rod or channel 204 of an object being imaged and transfer that light to the polarizer 252 of the imaging system 238. The beamsplitter 264 can be mounted within the endoscope 200 at a Brewster's angle with such a mounting. The beamsplitter 264 in this example can form a 33.5° angle with respect to the long axis 272 of the rod.

The beamsplitter 264 can also form a 33.5° angle with respect to the central axis of the imaging system 238.

FIG. 12 also illustrates an image sensor 148 mounted within the base unit 202 of the endoscope 200. The image sensor 148 can be mounted within an image sensor housing 258 within the endoscope 200. The image sensor 148 can be attached to an electrical cable connector 254 whereby the cable connector 254 can attach to a cable 230 to provide image signal data from an object being imaged to an external unit. The external unit can be a television screen, for example. The image sensor 148 can be a charge coupled device (CCD). The CCD can be a ⅛ inch CCD. By using a ⅛ inch CCD, the user can quadruple the amount of light he receives from an image. When using a ⅛ inch CCD chip, the focal length of the endoscope 200 can be between 25 and 30 mm. Preferably the focal length is 27 mm.

FIG. 14 illustrates the rod tip 260 of the miniature endoscope 200 whereby the rod tip 260 includes the first object lens 208, the second object lens 210 and a dark coating or tube 214 around a rod 204. As shown, the rod tip 260 is mounted within a needle or cannula 240. Such insertion of the rod tip 260 within the cannula 240 can be done after the cannula 240 is inserted into a surgical site of interest. Once the rod tip 260 is placed in the cannula 240, the cannula 240 can lock on to the base unit 202 by means of a locking mechanism.

Figure 15:
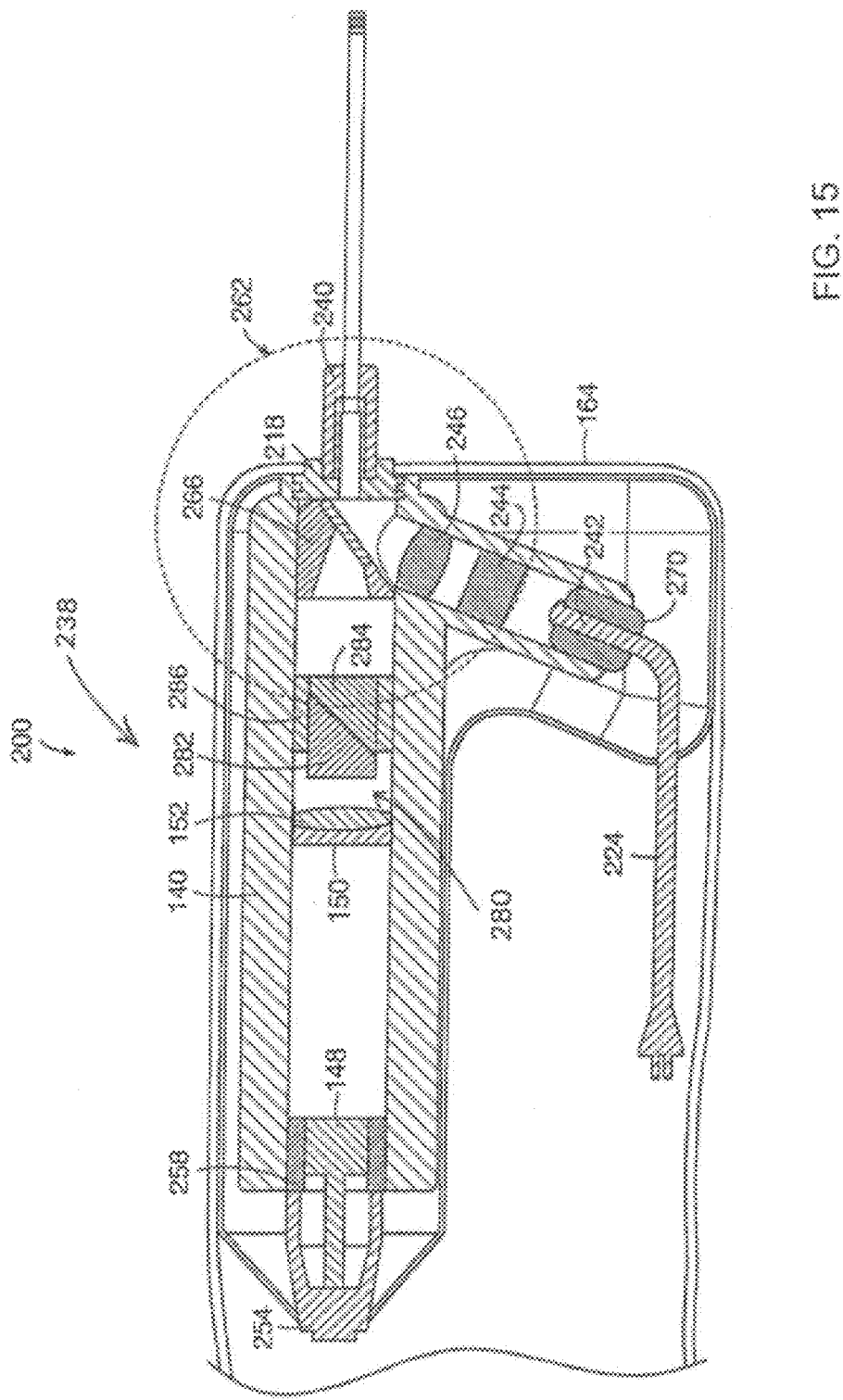
FIG. 15 shows a cross-sectional view of an alternate embodiment of an endoscope.
Figure 16:
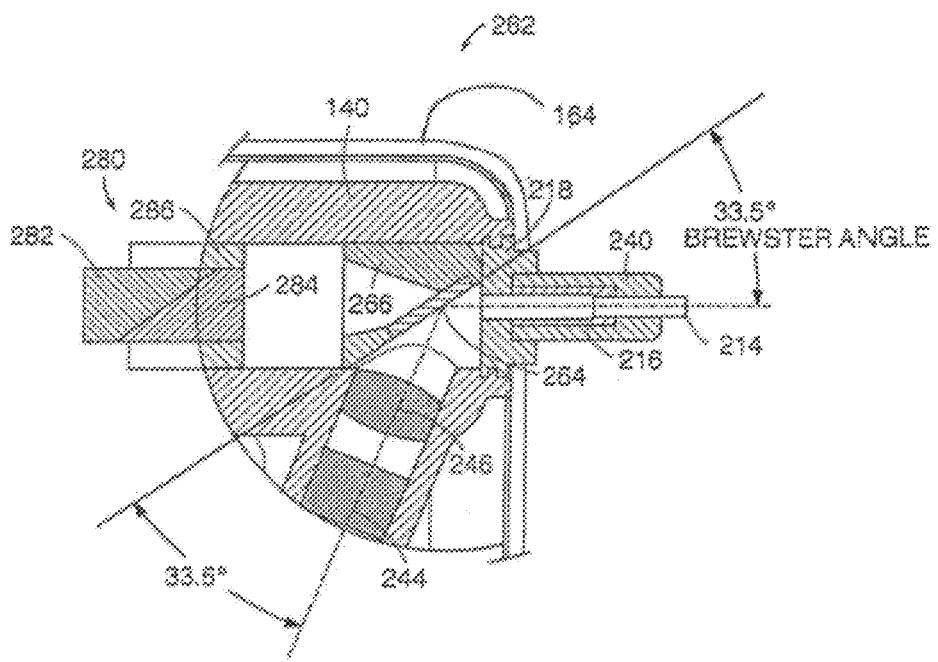
FIG. 16 shows a detailed view of the light transfer and imaging system of the endoscope of FIG. 15.

FIGS. 15 and 16 illustrate an alternate to the imaging system 238 illustrated in FIGS. 12, 13 and 14. The imaging system 238 can include a first image path lens 150, a second image path lens 152 and a polarizer 280. The cross polarizer 280 can be made from cal cite and can eliminate back reflections created by the rod and lens assembly 162. The polarization purity of the cross polarizer can be between $10^{-5}$ and $10^{-6}$. The cross polarizer 280 can increase light throughout by 15% to 20%. The polarizer 280 can include a first prism 282 and a second prism 284. The polarizer 280 can be attached to the housing 140 of the endoscope 200 by a polarizer housing 286.

FIG. 16 illustrates the light transfer and imaging system 262 of FIG. 15. Light directed from the lens expander 246 can be sent through the beamsplitter 264 and into the rod 204 to an object being imaged. Light from the object being imaged can be transferred back through the rod 204 and through the prism 264 into the beamsplitter 280. The beamsplitter can transfer the image light to the polarizer 280 which can eliminate back reflections created by the object lenses 206.

Figure 17:
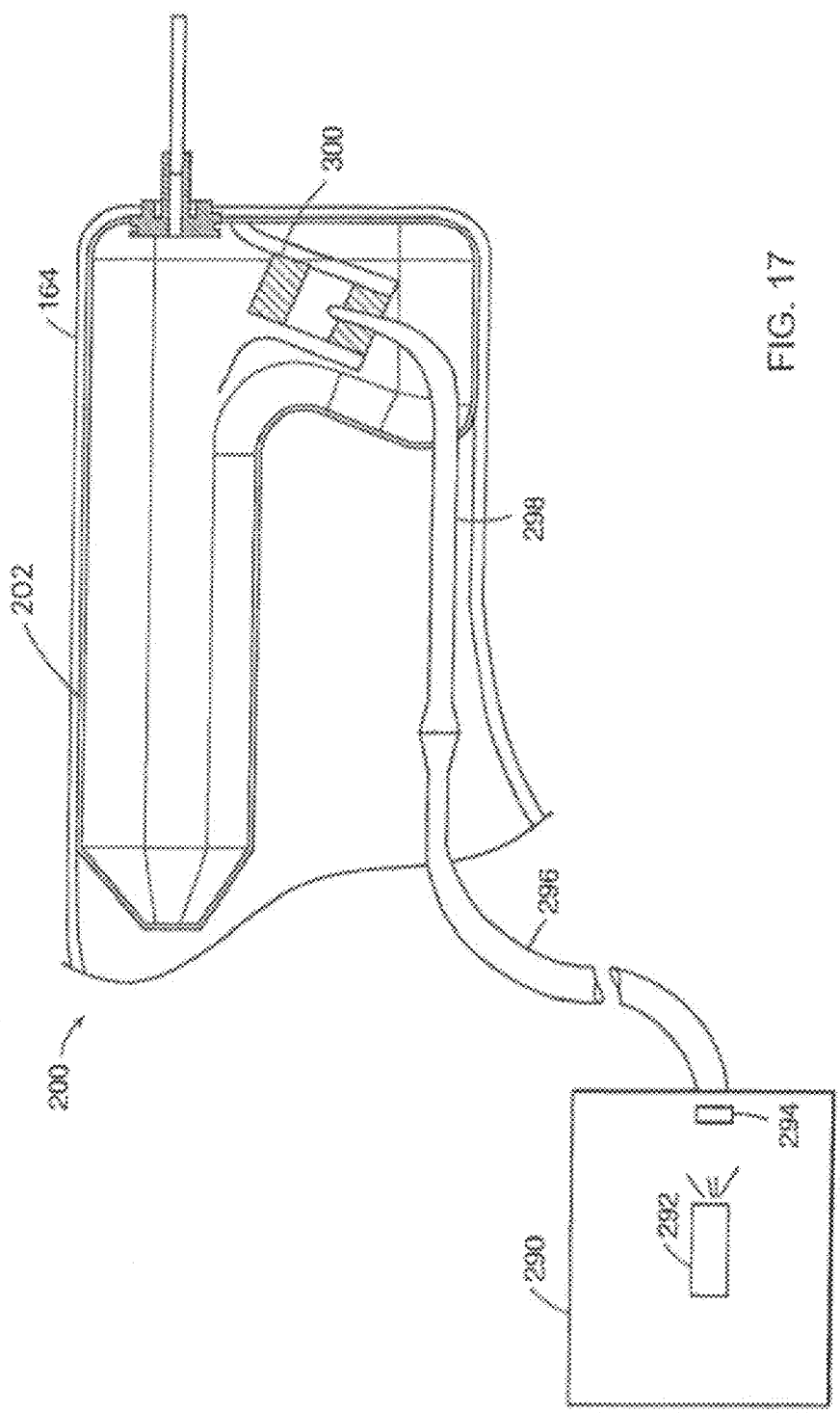
FIG. 17 shows a micro endoscope with an external light source.

FIG. 17 illustrates a miniature endoscope 200 where the light source of the endoscope 200 is an external light source 290. The external light source can include a lamp 292 and light source optics 294. The lamp 292 can be a xenon lamp which can be 300 watts, for example. The optics 294 and lamp 292 of the external light source 290 can be coupled to the miniature endoscope 200 by a silica cable 296. The endoscope 200 can include a reducer 298 mounted within the base unit 202. The reducer 298 can reduce the cross sectional area of the source by a factor of 2-5 times. Preferably the reducer reduces by a factor of 3.5. When used with a xenon source, the reducer 298 can reduce the aperture size of source for efficient coupling into the probe waveguide. The use of a reducer 298 within the endoscope 200 can simplify the optics within the lighting system 236.

Figure 18:
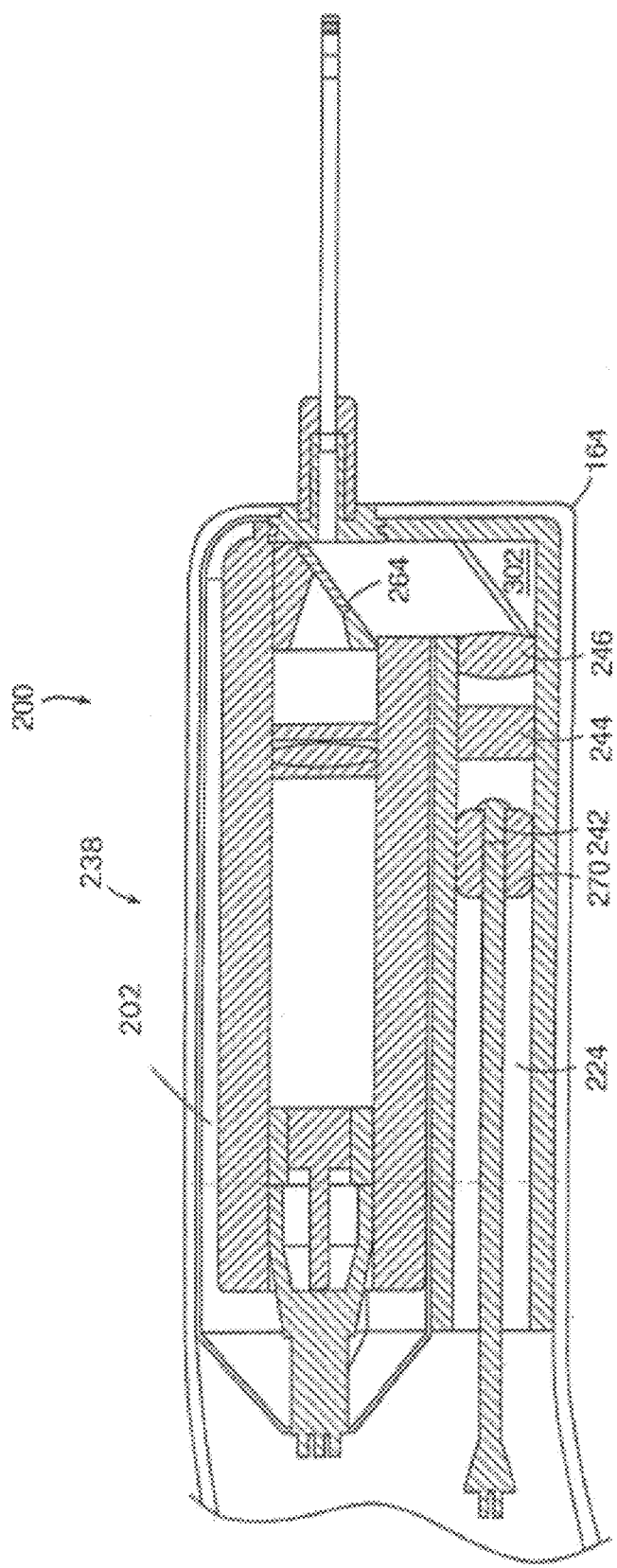
FIG. 18 illustrates an alternate configuration of a lighting system for a miniature endoscope.

FIG. 18 shows a configuration of the endoscope 200 wherein the lighting system 236 is mounted within the base unit 202 parallel to the imaging system 238. With such a configuration, the lighting system 236 can include a mirror 302. The mirror 302 can be a fold mirror for example. The mirror 302 can be mounted within the endoscope 200 such that light from a light source 242 which travels through a polarizer 244 and an expander 246 can reflect from the mirror to travel to the prism 264.

FIG. 19 illustrates the cross section of a needle 240 wherein the needle acts a reducer to provide light to an object being imaged. The needle 240 can include an aperture 304. The aperture can be surrounded by a first cladding layer 306, an illumination channel 308 and a second cladding layer 310. The first cladding layer can have a first cladding layer thickness 312. The illumination channel 308 can include a channel thickness 314 which can be 10 microns. The second cladding layer 310 can include a second cladding thickness 316 whereby the thickness can be 3 microns.

FIG. 20 illustrates a cannula 240 having a stylet. Prior to inserting a needle 240 into a surgical site, a stylet or obturator can be inserted within the needle 240. The stylet can include a cutting surface 322 and a cleaning edge 324. When the stylet 320 and needle 240 are inserted into a surgical site, tissue can accumulate in an area between the stylet 320 and the needle 240. In order to eliminate this material from the area, the stylet 320 can include a cleaning edge 324 whereby the cleaning edge is formed of a less stiff material than is the cutting edge 322. When the stylet 320 is pulled towards the user after insertion of the needle 240 in the surgical site, the weaker edge or the cleaning edge 324 will bend about the needle thereby cleaning or wiping away any tissue debris from the needle area. Such a cleaning function allows proper insertion of the microendoscope within the cannula and proper viewing of a surgical site.

FIG. 21 shows a miniature endoscope 400 in side perspective view. The endoscope 400 includes a base unit 402 and a sheath assembly 404. The base unit 402 includes an electrical connection 406 for the imaging device, such as a CCD and a fiber optic light source connection 408.

The sheath assembly 404 includes a sterile barrier 410 and a rod and lens assembly 412. The sterile barrier 410 and the rod and lens assembly 412 are attached to a mounting hub 414, which is secured to the base unit 402 of the endoscope 400. The mounting hub 414 is a light sheath hub with luer lockside port.

The hub 414 can include an interface connection 416 that allows the sheath assembly 404 to attach to the base unit 402. The interface connection 416 can be a securing mechanism such as a locking mechanism. The sterile barrier 410, as seen in FIG. 22, is attached to the mounting hub 414 by bonding. The bonding can include cementing between the sterile barrier 410 and the hub 414, for example.

The mounting hub 414 can include a locking mechanism 418 such as a luer lock or fitting for example. The locking mechanism 418 can allow connection between the miniature endoscope 400 and a needle such as a 14 gage cannula, for example (manufactured by Popper).

Referring to FIG. 22, a sectional view of the endoscope 400 is shown. The sheath assembly 404 with the rod and lens assembly 412 and sterile barrier 410 is shown. The sterile barrier 410 and the rod and lens assembly 412 are attached to the mounting hub 414. The mounting hub 414 has a fiber optic window 420 which transmits light from a light source to a light sheath in an obturator. The window 420 can be a lens.

Still referring to FIG. 22, the rod and lens assembly 412 has a darkened outer tube 422 and a pair of object lenses 424. The distal end of the rod and lens assembly 412 will be discussed in further detail with reference to FIG. 27B.

Referring to FIG. 23, the base unit 402 of the endoscope 400 has a main scope body 428 with the CCD camera 430, a set of lenses 432, and a fiber optic tip mount 434 and fiber optic bundle 436 which define an opening 438 through which an optical image passes from the rod and lens assembly 412 towards the CCD camera 430. The opening 438 can be covered by a window or a lens. Still referring to FIG. 23, underlying the main scope by 428 is a fiber optic 442 which extends from the fiber optic light source connection 408 to fiber optic bundle 436.

Figure 24:
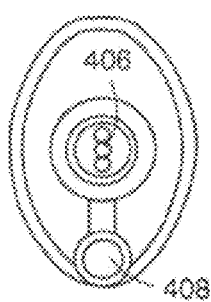
FIG. 24 is a rear view of the miniature endoscope.

FIG. 24 shows the rear portion of the base unit 402 of the endoscope 400. The electrical connection 406 is seen and in addition the fiber optic light source connection 408 is shown.

Figure 25A:
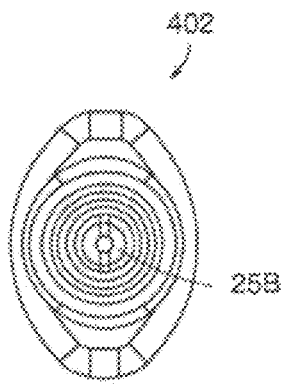
FIG. 25A is a front view of the base of the miniature endoscope with the needle not attached.
Figure 25B:
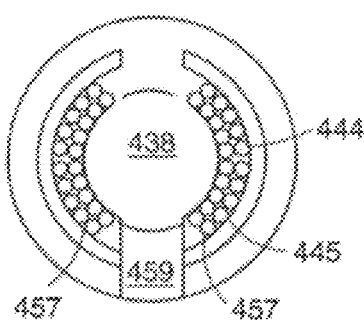
FIG. 25B is an enlarged view of a portion of the connection of the endoscope of FIG. 25A.

Referring to FIG. 25A, a front view of the base unit 402 is shown with the sheath assembly 404 removed. The base unit 402 has a plurality of fiber optic fibers 444 forming an annulus 445 surrounding the opening 438 as seen in FIG. 25B. The fiber optic bundle 436 is formed of these fiber optic fibers 444 in one embodiment. Alternately, the fiber optic bundle 436 has a single fiber optic fiber. The annulus 445 can be a continuous circular pattern. Alternately, the annulus is formed of two semicircular portions 457. A slot 459 can separate the semicircular portions 457. The slot 459 can allow mechanical attachment of the light sheath 422, shown in FIG. 27B to the hub 446.

Referring to FIG. 26, a side sectional view of the endoscope 400 is shown. The main scope body 428 as indicated above, has the CCD camera 430 which is connected through the electrical connection 406 to a monitor, such as illustrated in FIG. 1. The CCD camera 430 captures the image projected through the set of lenses 432 that is projected from the high index glass rod of the sheath assembly 404. While the sheath assembly is solid, the image that is projected through the lens 432 in the main scope body is through the opening 438. To light the image, the fiber optics 442 directs the light from the fiber optic light source connection 408 to the fibre optic bundle 436. The fiber optic bundle 436 can be formed of a plurality of fiber optics or from a single fiber optic.

Referring to FIG. 27A, the fiber optic bundle 436 projects its light through the lens 432 into the light sheath 448. The lens 432 can be a window, in an alternate embodiment. The connector between the bundle 436 and the lens 432 is shown in FIG. 29A.

The disposable optic tube hub connector 446 with lens 432 can attach to an obturator or needle having a flushing port 450, as shown in FIG. 26. The flushing port 450 can include a cap 452. The flushing port 450 allows a user the ability to flush a needle, after insertion into a surgical site, either when the rod and lens assembly 412 is located within the needle or has been removed from the needle. A fluid source, such as a syringe filled with saline, for example, can be attached to the port 450. When a user flushes the needle with saline while the rod and lens assembly 412 is located within the needle, the endoscope can block fluid from flowing from a proximal end of the needle, thereby concentrating flow through a distal end located within a surgical site. Alternately, for a user to flush the needle without the rod assembly 412 within the needle, the cap 452 can be used to cover the proximal end of the needle to direct the flow of the fluid to the distal end of the needle. Such flushing can allow clear viewing of a surgical site.

Referring to FIG. 27B, the distal end of the sheath assembly 404 has the light sheath 448 and encircles the disposable optic dark tube 422 containing the object lenses 424. Light can be transferred from the fiber optic bundle 436 through the light sheath and to an object being imaged.

Figure 28:
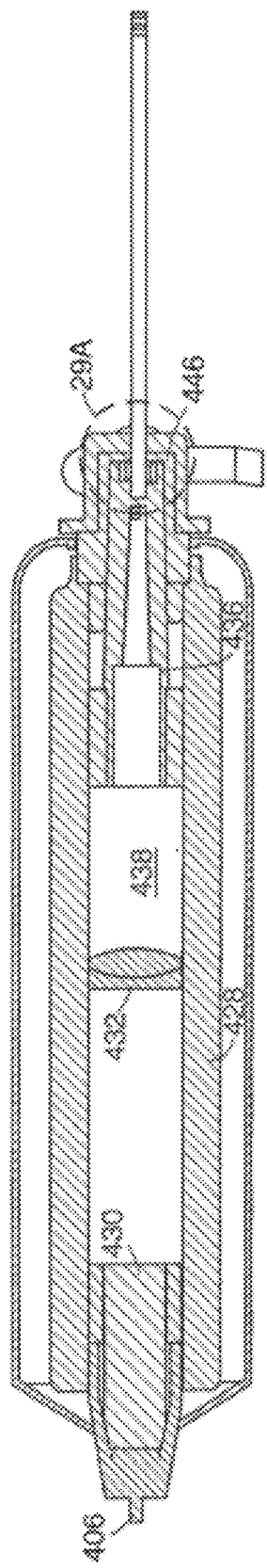
FIG. 28 is a sectional view of the miniature endoscope taken along the line 28-28 of FIG. 26.

FIG. 28 is a sectional view taken along the line 28-28 of FIG. 26. The figure shows a sectional view of the main scope body 428 cut through and looking up from the optical opening 438. The CCD 430 with connection 406 is shown. Likewise the lens 432 through which the image project are shown.

The fiber optic bundle 436, through which light is passed from the fiber optic 442, as shown in FIG. 26, encircles a portion of the optical opening 438 and directs light through the lens 432 in the disposable optics dark tube hub connector 446 into the light sheath surrounding the rod and lens assembly 412.

FIG. 29A is an enlarged sectional view of the interface of the fiber optic bundle 436, the disposable optics dark tube hub connector 446 and the mounting hub 414.

While this invention has been particularly shown and described with references to preferred embodiments thereof, it will be understood by those skilled in the art that various changes in form and details may be made therein without departing from the scope of the invention encompassed by the appended claims.

We claim:

1. A miniature endoscope for orthopedic imaging comprising:
    a probe for orthopedic diagnostic imaging, the probe including a fiber optic imaging waveguide that transmits an image, and having a diameter of less than 2 mm and a length between 2 cm and 10 cm, the probe having a mounting hub;
    a fiber optic illumination channel within the probe that is concentric about the optical waveguide, the illumination channel being positioned between an inner sheath and an outer sheath;
    a handle removeably attached to the mounting hub of the probe with a connector;
    a light source that is optically coupled to the fiber optic illumination channel with the mounting hub;
    a cannula that receives a distal end of the probe such that the outer sheath slides within the cannula, the cannula having a locking mechanism at a proximal end that attaches to the probe;
    a sterile barrier attached to the mounting hub and that can be extended over the handle;
    an optical lens coupled to a distal end of the waveguide;
    an optical relay mounted in the handle and that is optically coupled to a proximal end of the waveguide; and
    an imaging device mounted in the handle at a proximal end of the optical relay that receives an image from the optical waveguide.

2. The miniature endoscope of claim 1 wherein the endoscope has an outer diameter of 1.6 mm or less.

3. The miniature endoscope of claim 1 wherein the waveguide has an outer diameter between 0.6 and 1.6 mm.

4. The miniature endoscope of claim 1 wherein the illumination channel includes a binary phase ring which disperses light from the illumination channel.

5. The miniature endoscope of claim 1 wherein the waveguide comprises a glass having a refractive index in the range between 1.6 and 1.9.

6. The miniature endoscope of claim 1 wherein the waveguide comprises a glass rod.

7. The miniature endoscope of claim 1 wherein the optical waveguide further comprises a light absorbing layer having a thickness between 5 and 10 µm.

8. The miniature endoscope of claim 1 wherein the optical waveguide further comprises a light absorbing layer having an extramural absorption glass.

9. The miniature endoscope of claim 1 wherein the optical waveguide further comprises a light absorbing layer having a refractive index of 1.6 or less.

10. The miniature endoscope of claim 1 wherein the illumination channel has a wall thickness in a range of 0.1 mm and 0.2 mm.

11. The miniature endoscope of claim 1 wherein the illumination channel has a refractive index in a range between 1.4 and 1.6.

12. The miniature endoscope of claim 1 wherein the outer sheath comprises a metal tube.

13. The miniature endoscope of claim 12 wherein the outer sheath comprises a polyamide coating.

14. The miniature endoscope of claim 13 wherein the polyamide coating has a thickness between 100 and 150 μm.

15. The miniature endoscope of claim 1 wherein the optical relay comprises one or more lenses.

16. The miniature endoscope of claim 1 wherein the optical lens comprises a plastic lens.

17. The miniature endoscope of claim 1 wherein the imaging device comprises a charge coupled device.

18. The miniature endoscope of claim 1 wherein the cannula further comprises a distal needle that penetrates tissue.

19. The miniature endoscope of claim 1 further comprising a display connected to the imaging device.

20. The miniature endoscope of claim 1 wherein the illumination channel is optically coupled to a light source with a lens in the handle.

21. The miniature endoscope of claim 1 further comprising an optical coupler that optically connects the light source to the illumination channel.

22. The miniature endoscope of claim 1 wherein the cannula further comprises a fluid delivery port.

23. The miniature endoscope of claim 22 wherein the barrier is attached to a rigid waveguide housing that is connected to the handle.

24. The miniature endoscope of claim 1 wherein the light source comprises a lamp within the handle that is optically coupled to the illumination channel.

25. The endoscope of claim 1 further comprising a tube around the optical waveguide and an outer tube around the fiber optic illumination channel.

26. The endoscope of claim 25 wherein the outer tube is a plastic material.

27. The endoscope of claim 25 wherein the tube comprises a metal.

28. The endoscope of claim 1 wherein the endoscope probe has a length to diameter ratio between 40:1 and 60:1.

29. The endoscope of claim 1 further comprising a computer connected to the imaging device.

30. The endoscope of claim 29 further comprising an image processing sequence.

31. The endoscope of claim 30 wherein the image processing sequence subtracts a stored light distribution pattern from a video image.

32. The endoscope of claim 31 wherein the stored light distribution pattern corresponds with a light reflection pattern for the endoscope.

33. The endoscope of claim 1 wherein the concentric illumination channel has a thickness of 10 microns.

34. The endoscope of claim 1 wherein the concentric illumination channel has a thickness of 30 microns.

35. A miniature endoscope for orthopedic imaging comprising:
    a probe for orthopedic diagnostic imaging, the probe including a fiber optic imaging channel having a diameter in a range of 0.6 mm to 1.6 mm and the probe having a diameter less than 2 mm and a mounting hub;
    a tube surrounding the imaging channel;
    a fiber optic illumination channel within the probe that is concentric about the tube and the imaging channel and a light source that is optically coupled to the fiber optic illumination channel with the mounting hub attached to the handle, the illumination channel having a thickness in a range of 0.1 mm to 0.2 mm;
    an outer tube around the fiber optic illumination channel;
    a handle removably attached to the probe with a connector;
    a cannula that receives a distal end of the probe such that the distal end of the probe slides within the cannula, the cannula having a locking mechanism at a proximal end that attaches to the probe;
    a sterile barrier attached to the mounting hub that can be extended over the handle;
    a first lens and a second lens that are optically coupled to a distal end of the imaging channel;
    an optical relay mounted in the handle and optically coupled to a proximal end of the imaging channel; and
    an imaging device mounted in the handle and optically coupled to a proximal end of the optical relay.

36. The miniature endoscope of claim 35 wherein the imaging device comprises a charge coupled device.

37. The miniature endoscope of claim 35 wherein the imaging channel comprises a transparent material having a refractive index of at least 1.6.

38. The miniature endoscope of claim 37 wherein the imaging light channel comprises a glass rod.

39. The miniature endoscope of claim 38 wherein the glass rod comprises an F2 or an F7 glass.

40. The miniature endoscope of claim 35 further comprising a light absorbing layer around the imaging channel.

41. The miniature endoscope of claim 35 wherein the illumination channel is coupled to the light source with a fiber optic connector.

42. The miniature endoscope of claim 35 wherein the endoscope has a display connected to the imaging device for arthroscopic examination.

* * * * *